United States Patent
Inouye et al.

(10) Patent No.: US 12,114,952 B2
(45) Date of Patent: Oct. 15, 2024

(54) SYSTEMS AND METHODS FOR COUPLING MEDICAL COMPONENTS

(71) Applicant: Intuitive Surgical Operations, Inc., Sunnyvale, CA (US)

(72) Inventors: Matthew D. Inouye, Foster City, CA (US); Ruchi C. Bhatt, San Jose, CA (US); Timothy D. Boucher, Los Altos, CA (US); Benjamin G. Cohn, Oakhurst, CA (US); Peyman Taherkhani, San Francisco, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 700 days.

(21) Appl. No.: 17/319,486

(22) Filed: May 13, 2021

(65) Prior Publication Data
US 2022/0125539 A1   Apr. 28, 2022

Related U.S. Application Data

(60) Provisional application No. 63/025,066, filed on May 14, 2020.

(51) Int. Cl.
*A61M 16/04* (2006.01)
*A61B 34/00* (2016.01)
(Continued)

(52) U.S. Cl.
CPC .............. *A61B 34/71* (2016.02); *A61B 34/20* (2016.02); *A61B 34/37* (2016.02);
(Continued)

(58) Field of Classification Search
CPC ......... A61B 34/71; A61B 34/20; A61B 34/37; A61B 34/30; A61B 2034/2051;
(Continued)

(56) References Cited

U.S. PATENT DOCUMENTS 10,512,515 B2    12/2019   Bailey
2015/0297071 A1* 10/2015   Hung ............... A61B 1/267
                                                600/120
(Continued)

FOREIGN PATENT DOCUMENTS

WO   WO-2018145100 A1   8/2018
WO   WO-2019018736 A2   1/2019
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Ankit D Tejani
*Assistant Examiner* — Joshua Brendon Solomon
(74) *Attorney, Agent, or Firm* — Haynes & Boone, LLP.

(57) ABSTRACT

A system may comprise a connection member configured to be connected to an anatomic orifice device. The anatomic orifice device may be configured for insertion into a patient. The system may also comprise a mounting bracket coupled to a robot-assisted medical system. The mounting bracket may also include a movable mounting component coupled to a fixed mounting component. The movable mounting component may have a first configuration for mounting to the connection member in a first engagement and a second configuration for mounting to the connection member in a second engagement. The connection member may be spaced apart from the fixed mounting component in the first engagement and may be in direct contact with the fixed mounting component in the second engagement.

25 Claims, 21 Drawing Sheets

(51) Int. Cl.
    *A61B 34/20*       (2016.01)
    *A61B 34/37*       (2016.01)
    *A61M 16/08*       (2006.01)
    *A61B 34/30*       (2016.01)

(52) U.S. Cl.
    CPC .... *A61M 16/0418* (2014.02); *A61M 16/0816* (2013.01); *A61B 2034/2051* (2016.02); *A61B 2034/301* (2016.02); *A61M 2209/082* (2013.01)

(58) Field of Classification Search
    CPc ...... A61B 2034/301; A61B 2034/2065; A61B 2034/2048; A61B 2034/2055; A61B 2034/2061; A61B 2560/0437; A61B 2017/00809; A61B 2017/00876; A61M 16/0418; A61M 16/0816; A61M 16/01; A61M 2209/082; A61M 2205/502
    See application file for complete search history.

(56)               References Cited

U.S. PATENT DOCUMENTS

2016/0184032 A1*   6/2016   Romo .................. B25J 9/1682
                                                        901/46
2020/0405419 A1   12/2020   Mao et al.
2021/0228289 A1*   7/2021   Rohr Daniel ...... A61B 1/00128

FOREIGN PATENT DOCUMENTS

WO     WO-2019027922 A1     2/2019
WO     WO-2019222003 A1    11/2019
WO     WO-2020150165 A1     7/2020

\* cited by examiner

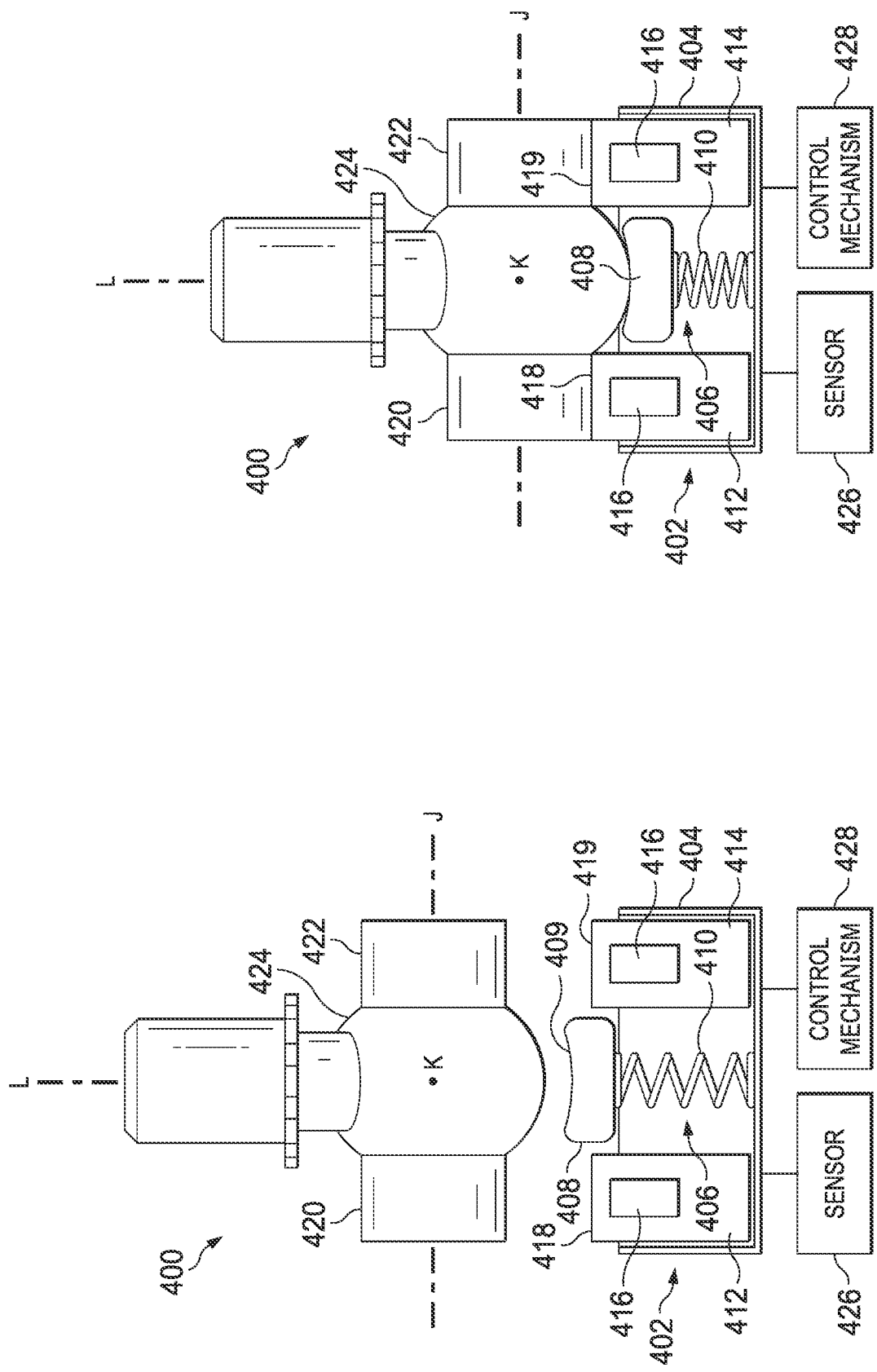

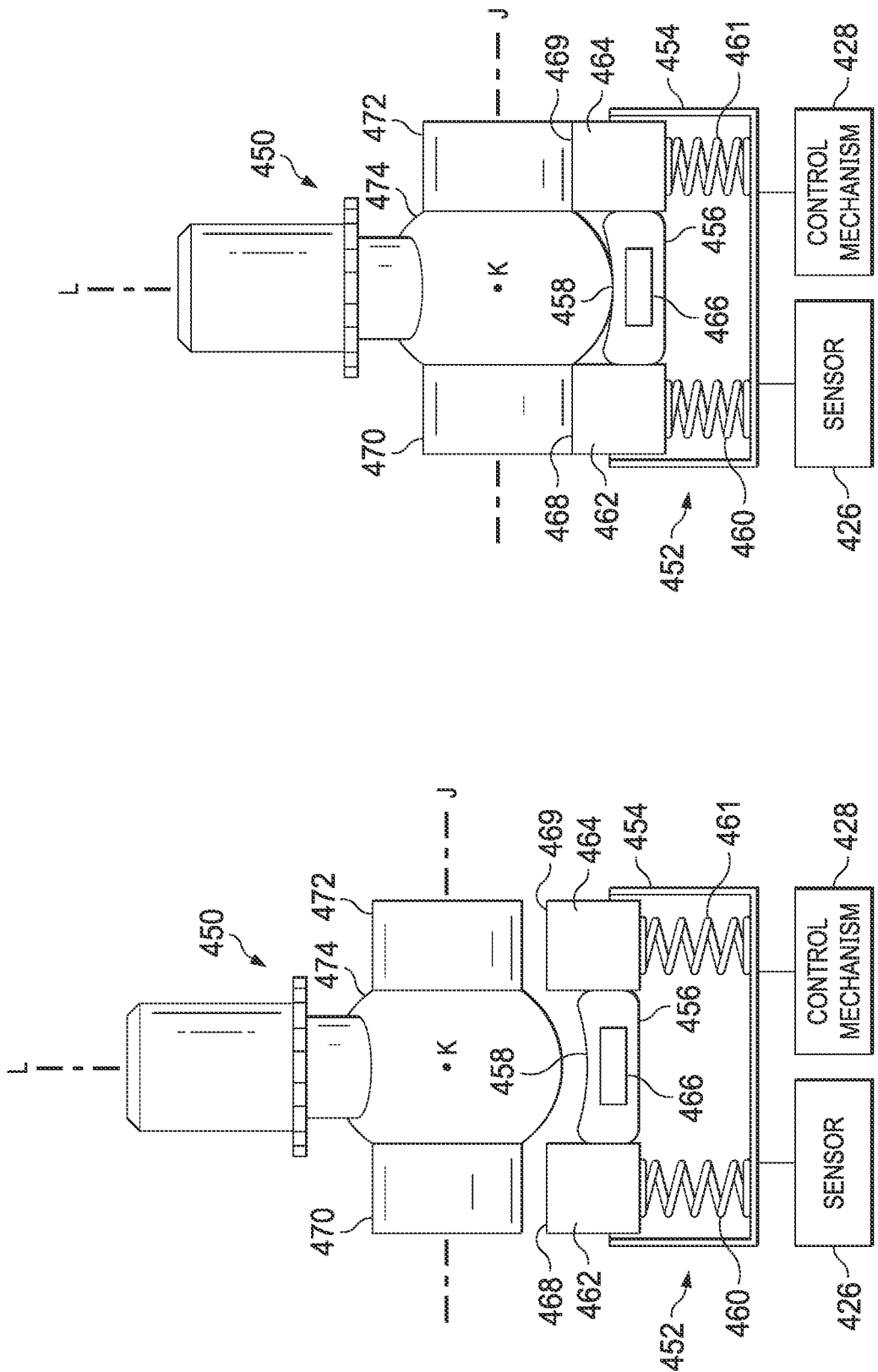

SYSTEMS AND METHODS FOR COUPLING MEDICAL COMPONENTS

CROSS-REFERENCE TO RELATED APPLICATIONS

This application claims the benefit of U.S. Provisional Application 63/025,066 filed May 14, 2020, which is incorporated by reference herein in its entirety.

FIELD

Examples described herein are related to systems and methods for coupling medical components with a patient anatomy to accommodate patient motion during a medical procedure.

BACKGROUND

Minimally invasive medical techniques may generally be intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions an operator may insert minimally invasive medical instruments to reach a target tissue location. Minimally invasive medical tools include instruments such as therapeutic instruments, diagnostic instruments, imaging instruments, and surgical instruments. Some minimally invasive techniques may use a flexible and/or steerable elongate device such as a flexible catheter that can be inserted into anatomic passageways and navigated towards a region of interest within the patient anatomy. Control of such an elongate device by medical personnel involves the management of several degrees of freedom including at least the management of insertion and retraction of the elongate device as well as steering of the device. Such control may be provided by a robot-assisted medical system.

In some examples, an anatomic orifice device, such as an endotracheal tube, may provide entryway management for the minimally invasive medical tool that is coupled to a robot-assisted medical system. The anatomic orifice device may also support the natural or surgically created orifice in the patient anatomy. Sometimes, unexpected patient motion may cause the anatomic orifice device to become displaced from the patient airway, which could result in loss of mechanical ventilation and/or damage to the patient's trachea. Thus, a connection between the anatomic orifice device and the robot-assisted medical system is desired that ensures patient safety during the medical procedure. Further, systems and techniques for coupling the anatomic orifice device and the robot-assisted medical system may promote efficiency and safety.

SUMMARY

The following presents a simplified summary of various examples described herein and is not intended to identify key or critical elements or to delineate the scope of the claims.

A system may include a connection member configured to be connected to an anatomic orifice device. The anatomic orifice device may be configured for insertion into a patient. The system may also include a sensor associated with a robot-assisted medical system. The sensor may be configured to sense a spatial relationship between a mounting bracket of the robot-assisted medical system and the connection member. The system may also include a controller configured to receive, from the sensor, an indication of the spatial relationship and determine, based on the indication of the spatial relationship, a mounting configuration of the mounting bracket with respect to the connection member. The controller may also command the robot-assisted medical system to move the mounting bracket into the mounting configuration.

A system may include a connection member configured to be connected to an anatomic orifice device. The anatomic orifice device may be configured for insertion into a patient. The system may also include a mounting bracket coupled to a robot-assisted medical system. The mounting bracket may include a movable mounting component coupled to a fixed mounting component. The movable mounting component may have a first configuration for mounting to the connection member in a first engagement and a second configuration for mounting to the connection member in a second engagement. The connection member may be spaced apart from the fixed mounting component in the first engagement and may be in direct contact with the fixed mounting component in the second engagement.

A system may include a connection member configured to be connected to an anatomic orifice device. The connection member may include a first partially spherical surface that includes a first engagement feature. The system may also include a mounting bracket coupled to a robot-assisted medical system. The mounting bracket may include a second partially spherical surface sized to receive the first partially spherical surface of the connection member. The second partially spherical surface may include a second engagement feature. The first partially spherical surface may be rotatable about a plurality of axes when the first partially spherical surface is received by the second partially spherical surface. The first engagement feature may be configured to engage the second engagement feature to restrict and/or guide motion of the connection member relative to the mounting bracket.

A system may include a connection member configured to be connected to an anatomic orifice device. The anatomic orifice device may be configured for insertion into a patient. The connection member may include a first magnetic connection ring and a second magnetic connection ring. The first and second magnetic connection rings may be coupled by a flexible member so that the first magnetic connection ring is moveable relative to the second magnetic connection ring. The system may also include a mounting bracket coupled to a robot-assisted medical system. The mounting bracket may be configured to magnetically attract and engage the first and second magnetic connection rings.

A system may include a connection member configured to be connected to an anatomic orifice device. The anatomic orifice device may be configured for insertion into a patient. The system may also include a mounting bracket coupled to a robot-assisted medical system and a docking guide configured to arrange the connection member in a predetermined configuration. The robot-assisted medical system may be configured to transfer the mounting bracket into engagement with the connection member while the connection member is in the predetermined configuration.

A system may include a connection member configured to be connected to an anatomic orifice device. The anatomic orifice device may be configured for insertion into a patient. The system may also include a mounting bracket coupled to a robot-assisted medical system and a tether coupled to the connection member and coupled to the mounting bracket. The tether may be retractable to draw the mounting bracket into contact with the connection member.

A system may include a connection member configured to be connected to an anatomic orifice device. The anatomic orifice device may be configured for insertion into a patient. The connection member may include includes an alignment feature. The system may also include a mounting bracket coupled to a robot-assisted medical system and a guidance member extending from the mounting bracket. The guidance member may be configured to align with the alignment feature to arrange the mounting bracket in a mating orientation for coupling the mounting bracket with the connection member.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIGS. 5A and 5B illustrate a connection member and a mounting bracket including a biasing member according to some examples.

FIGS. 6A and 6B illustrate a connection member and a mounting bracket including a biasing member according to some examples.

Figure 10B:
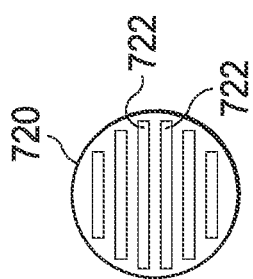
Figure 10C:
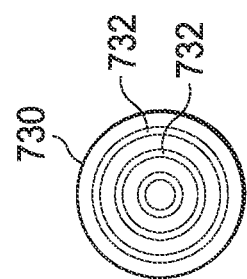
Figure 10A:
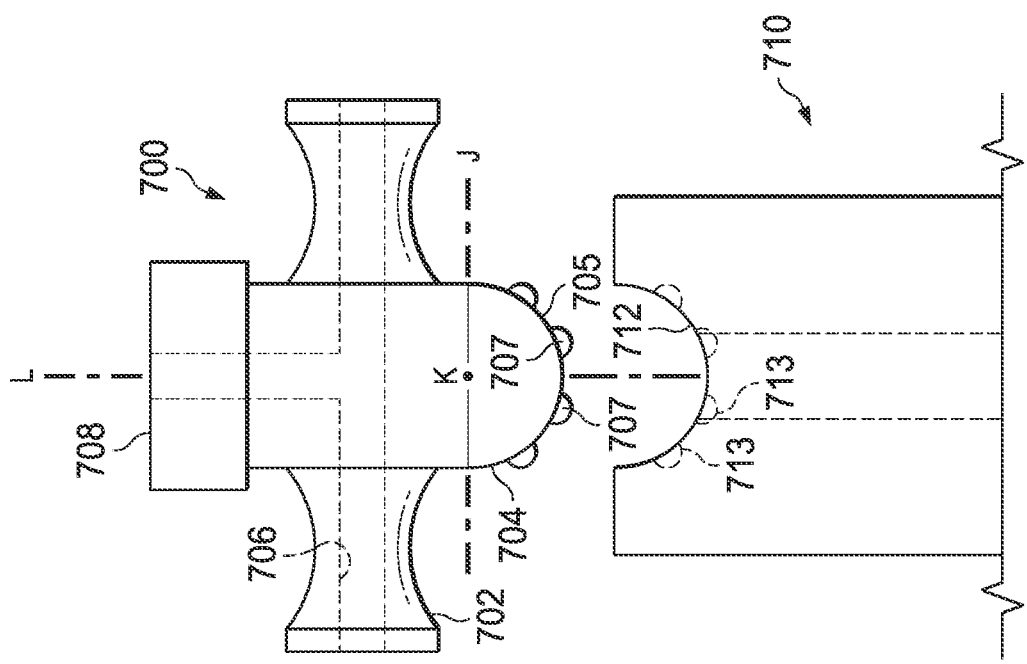

FIGS. 10A, 10B, and 10C illustrate a connection member and mounting brackets with an at least partially spherical surface and a variety of engagement features according to some examples.

Figure 11A:
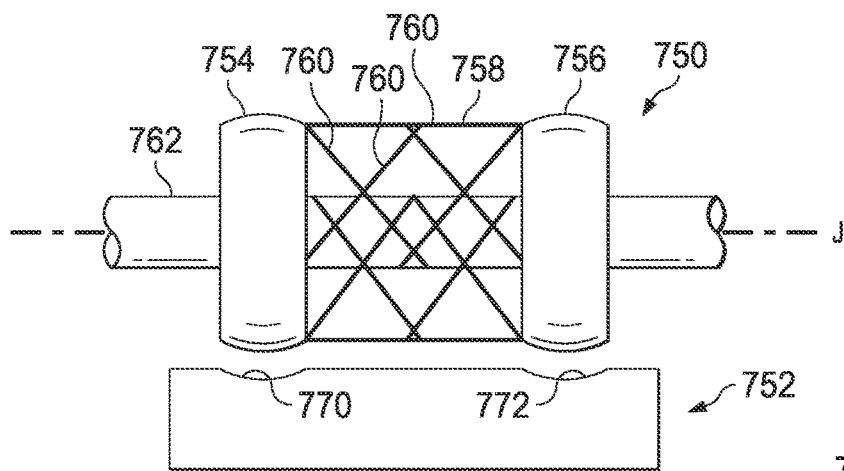
Figure 11B:
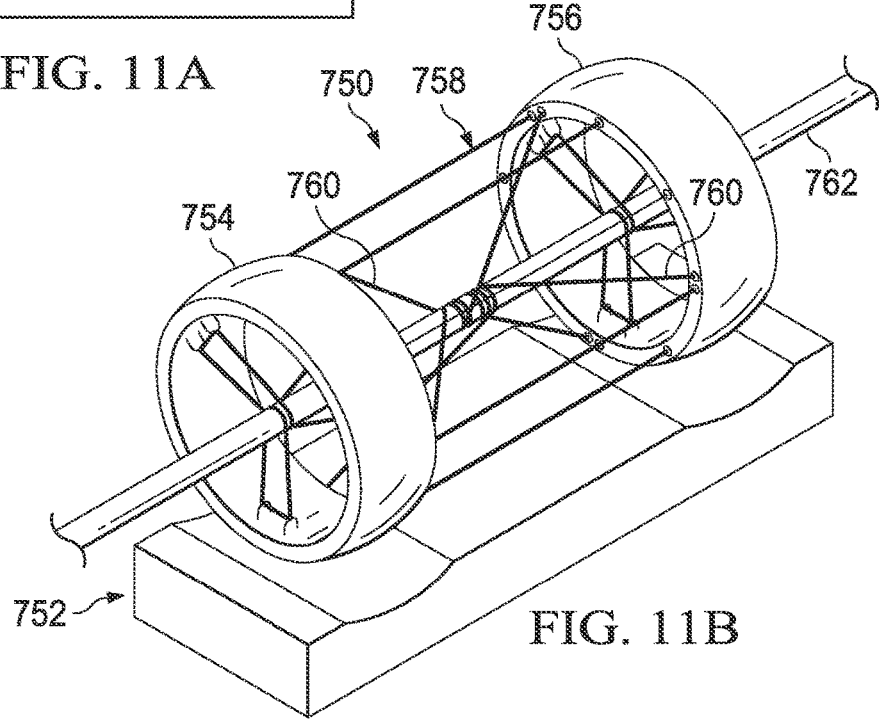

FIGS. 11A and 11B illustrate a mounting bracket and a connection member including a flexible member and according to some examples.

Figure 12:
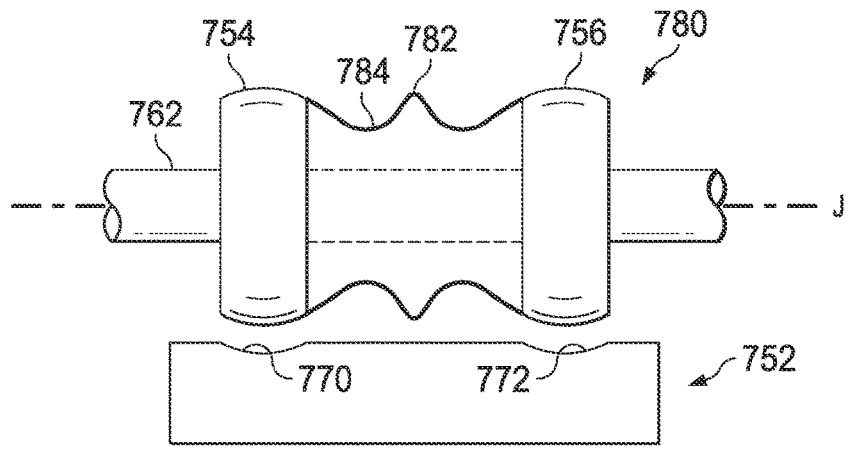

FIG. 12 illustrates a mounting bracket and a connection member including a flexible member according to some examples.

Figure 13A:
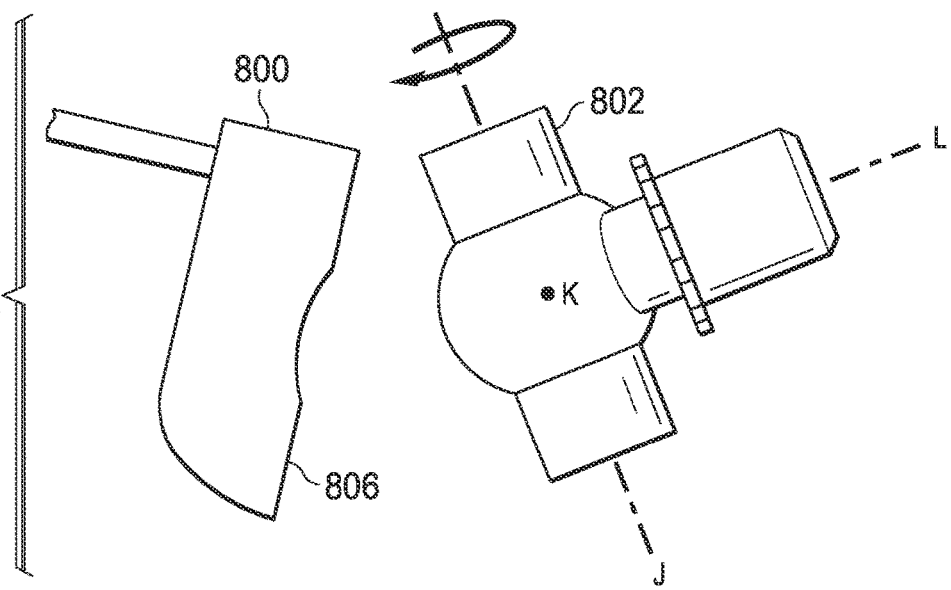
Figure 13B:
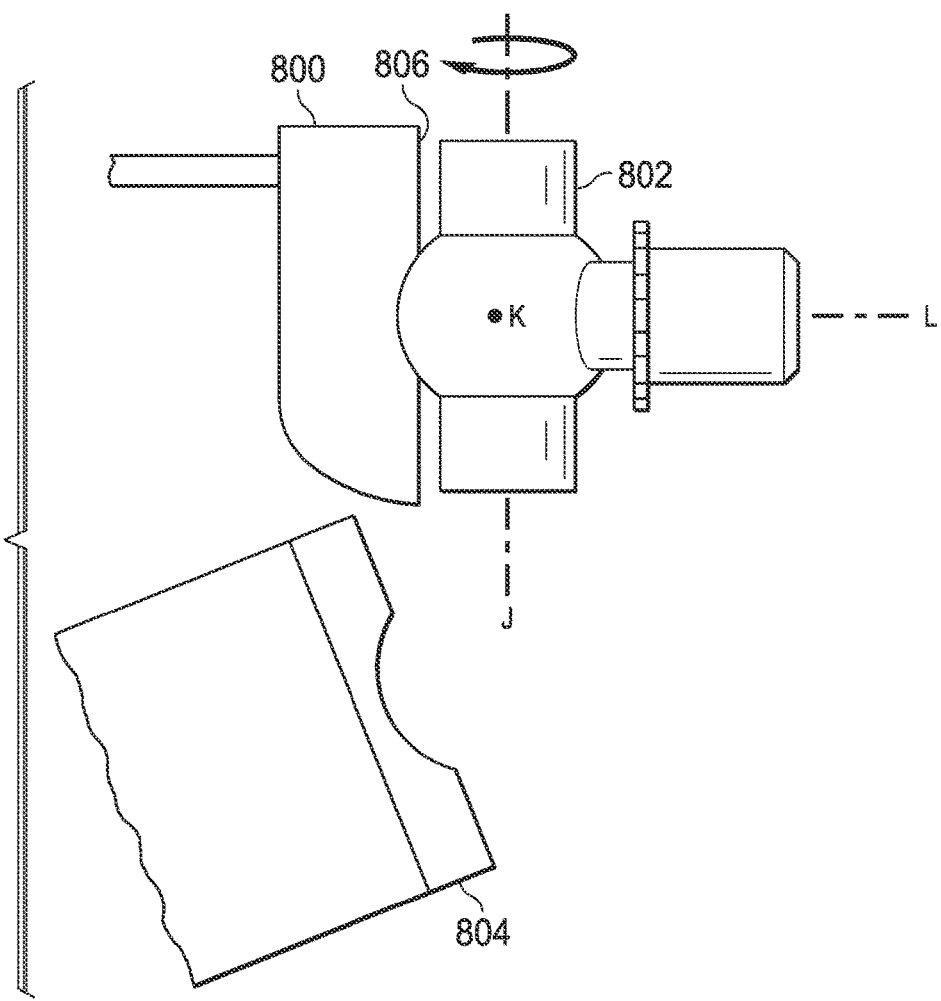
Figure 13C:
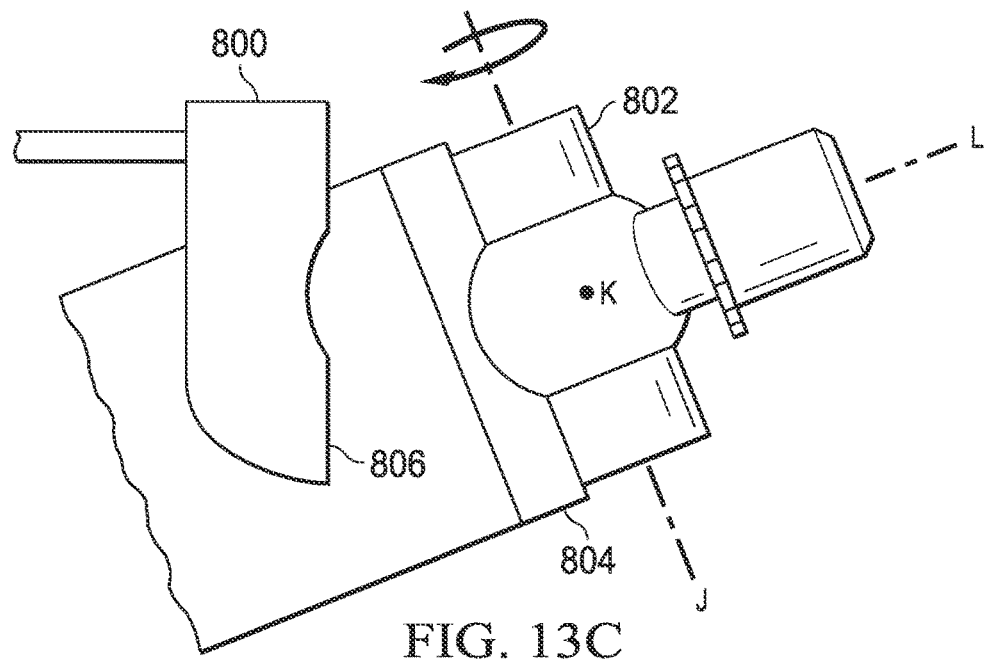

FIGS. 13A, 13B, 13C illustrate an alignment guide for orienting a connection member in preparation for mounting with a mounting bracket according to some examples.

Figure 14:
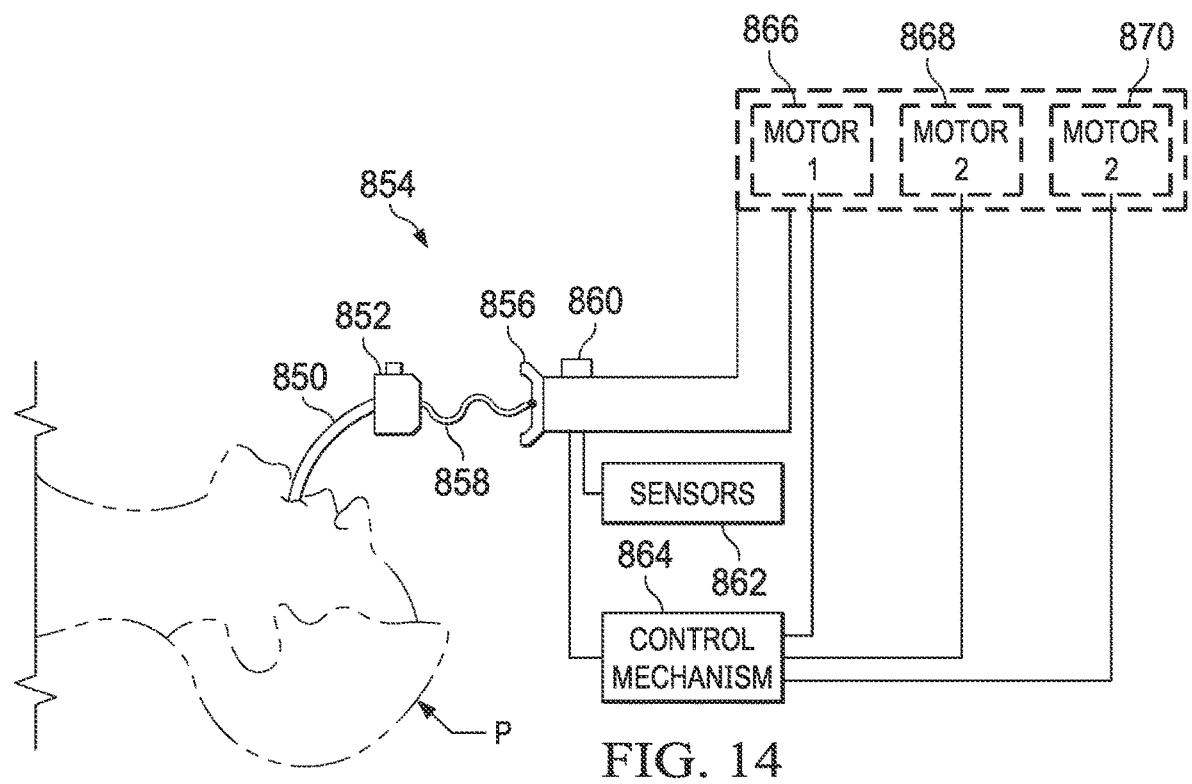

FIG. 14 illustrates a side view of patient with an anatomic orifice device tethered to a mounting bracket according to some examples.

Figure 15A:
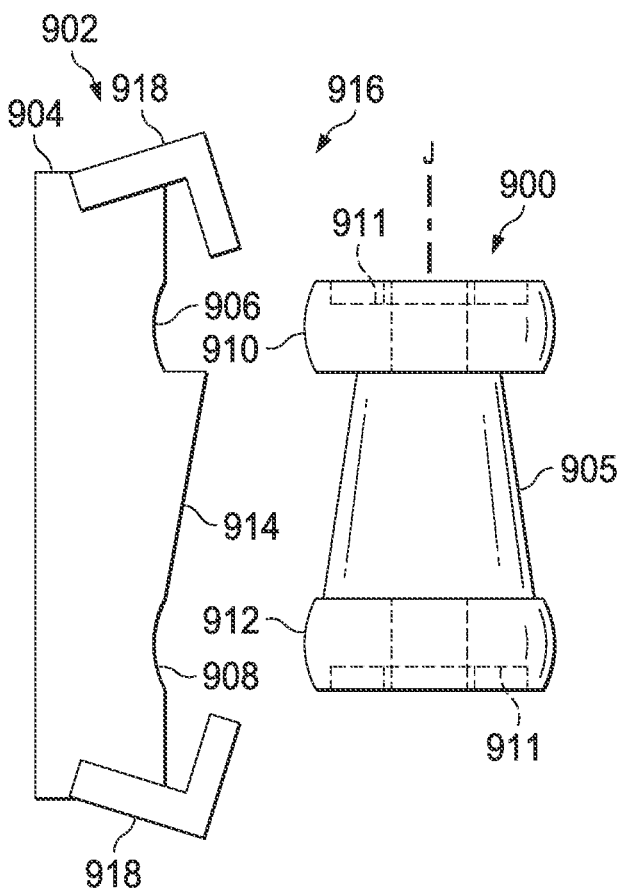
Figure 15B:
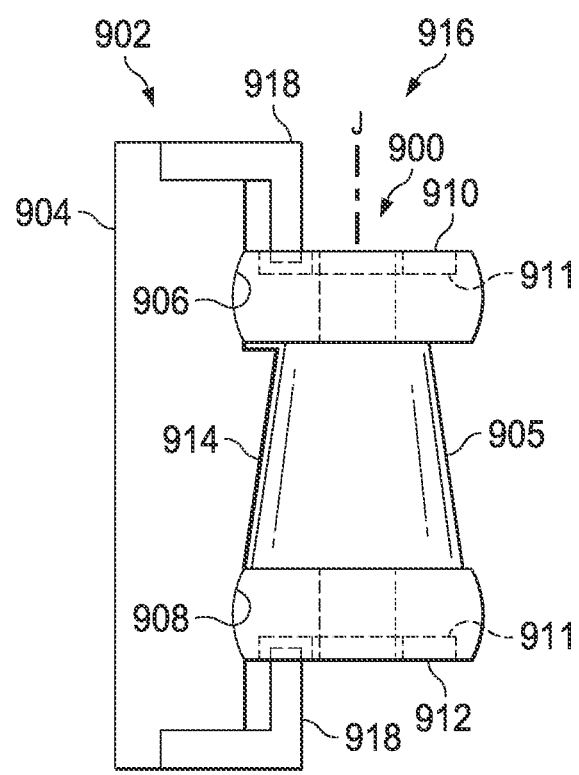

FIGS. 15A and 15B illustrate a side view of a connection member and a mounting bracket according to some examples.

Figure 16:
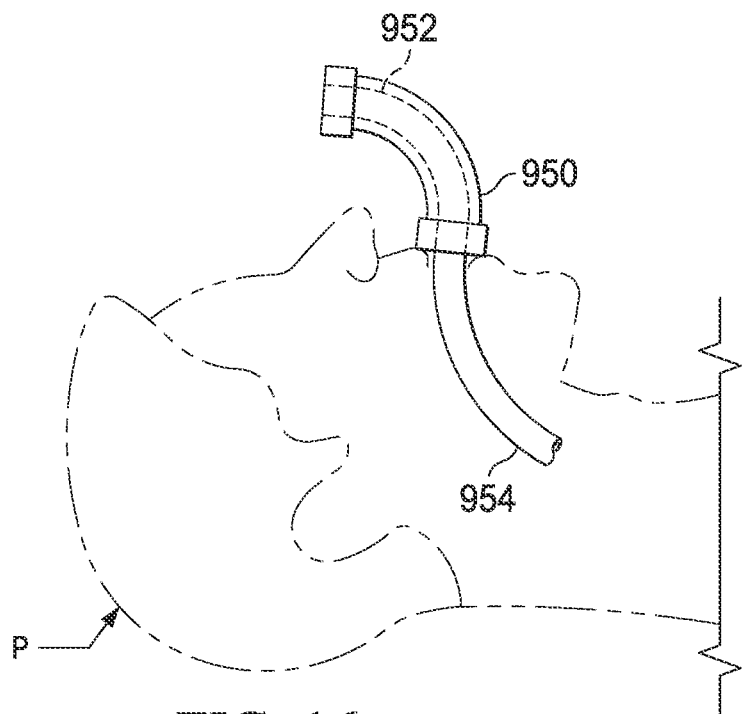

FIG. 16 illustrates a sleeve mounted to a proximal end of an anatomic orifice device according to some examples.

Figure 17:
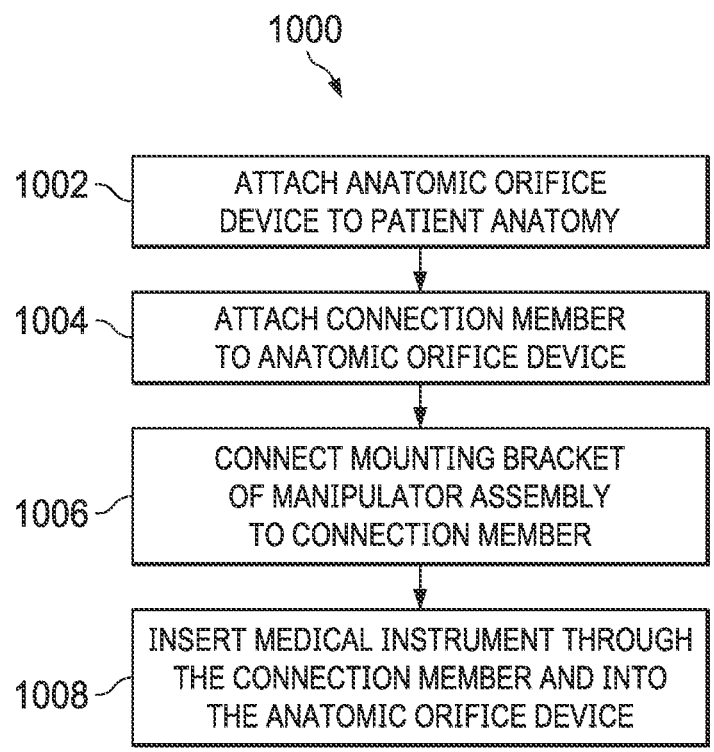

FIG. 17 is a flowchart illustrating an example method of connecting a patient to a medical instrument controlled by a manipulator assembly according to some examples.

Figure 18A:
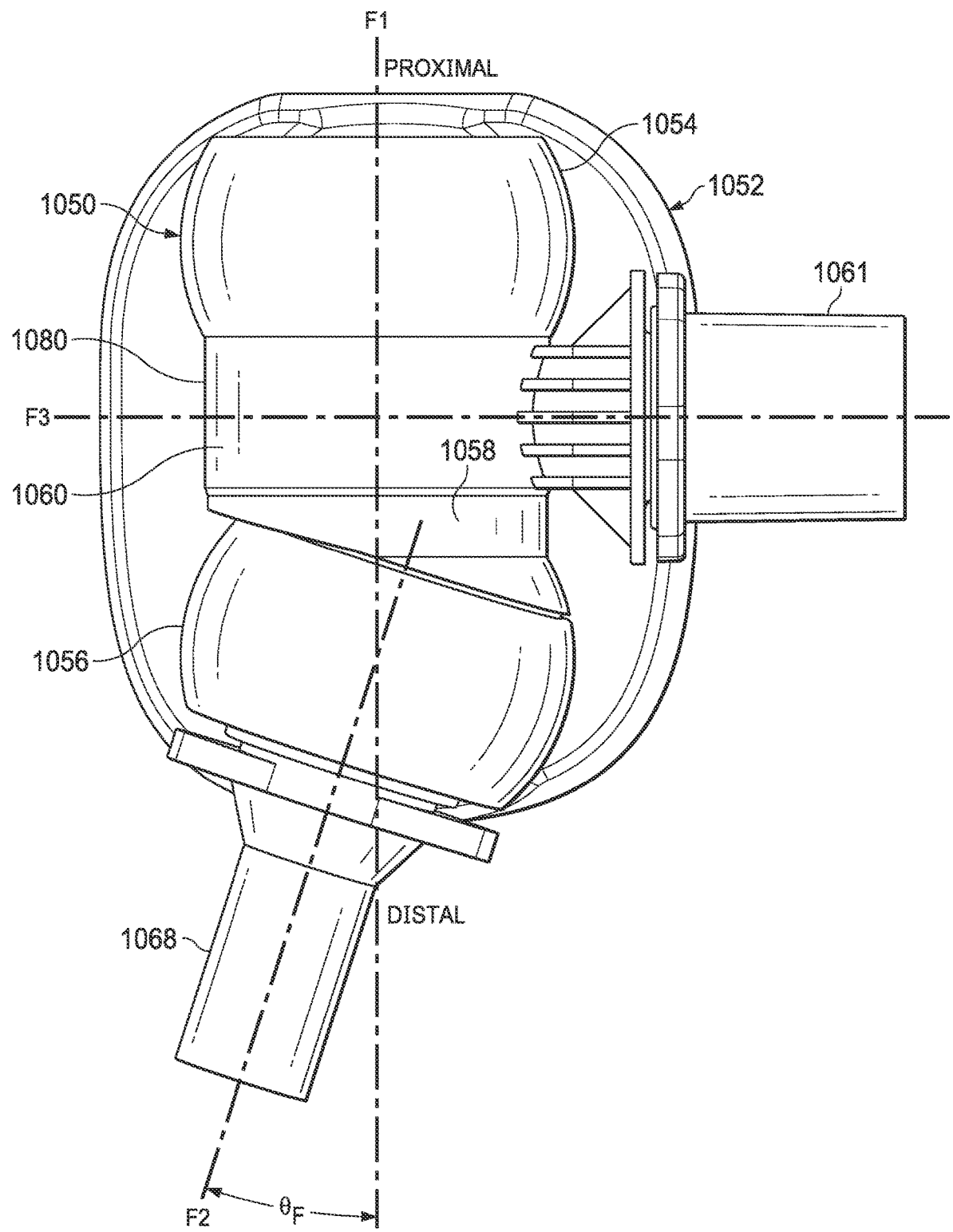

FIG. 18A illustrates a connection member and a mounting bracket according to some examples.

Figure 18B:
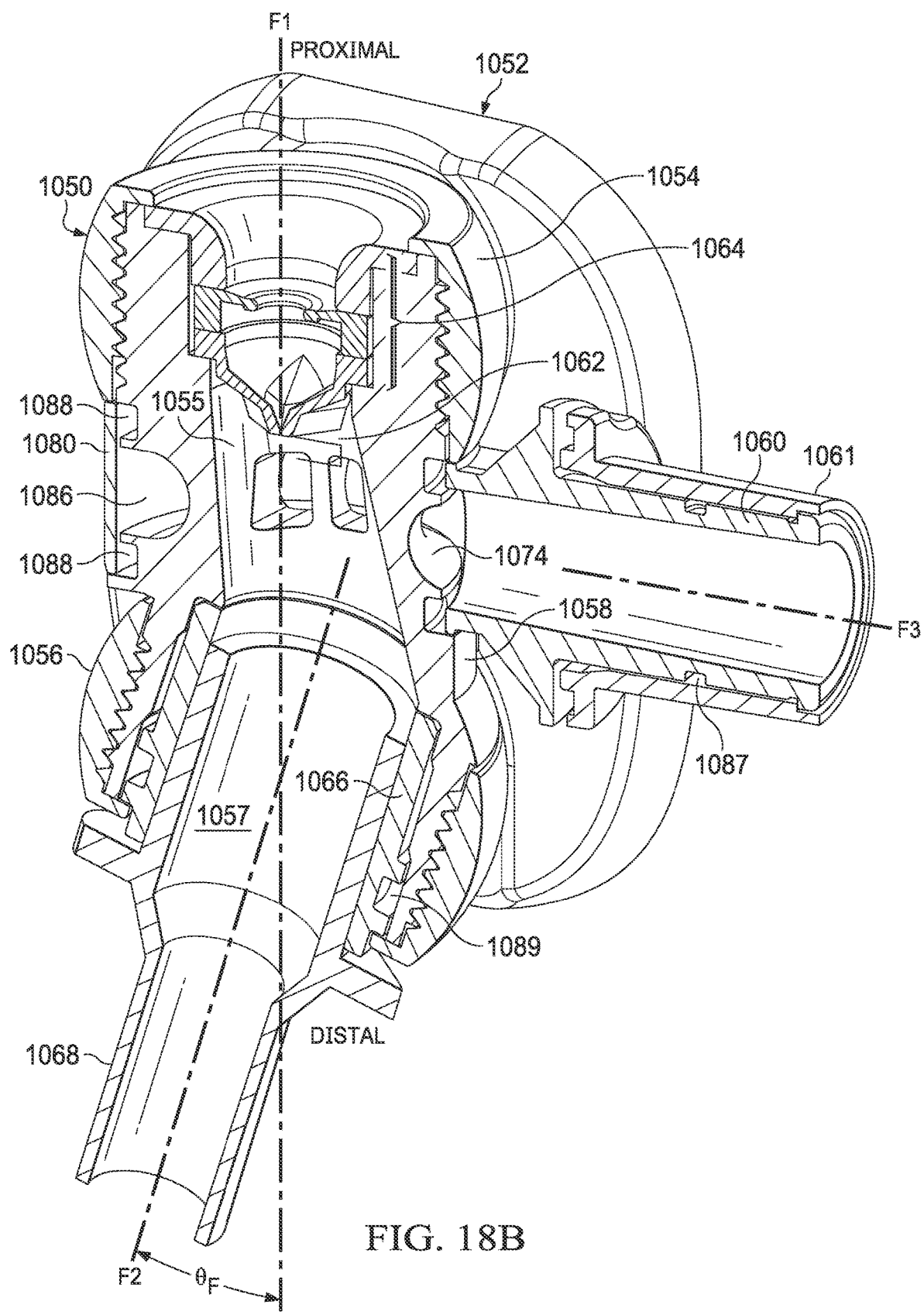

FIG. 18B illustrates a cross-sectional view of the connection member of FIG. 18A according to some examples.

Figure 19:
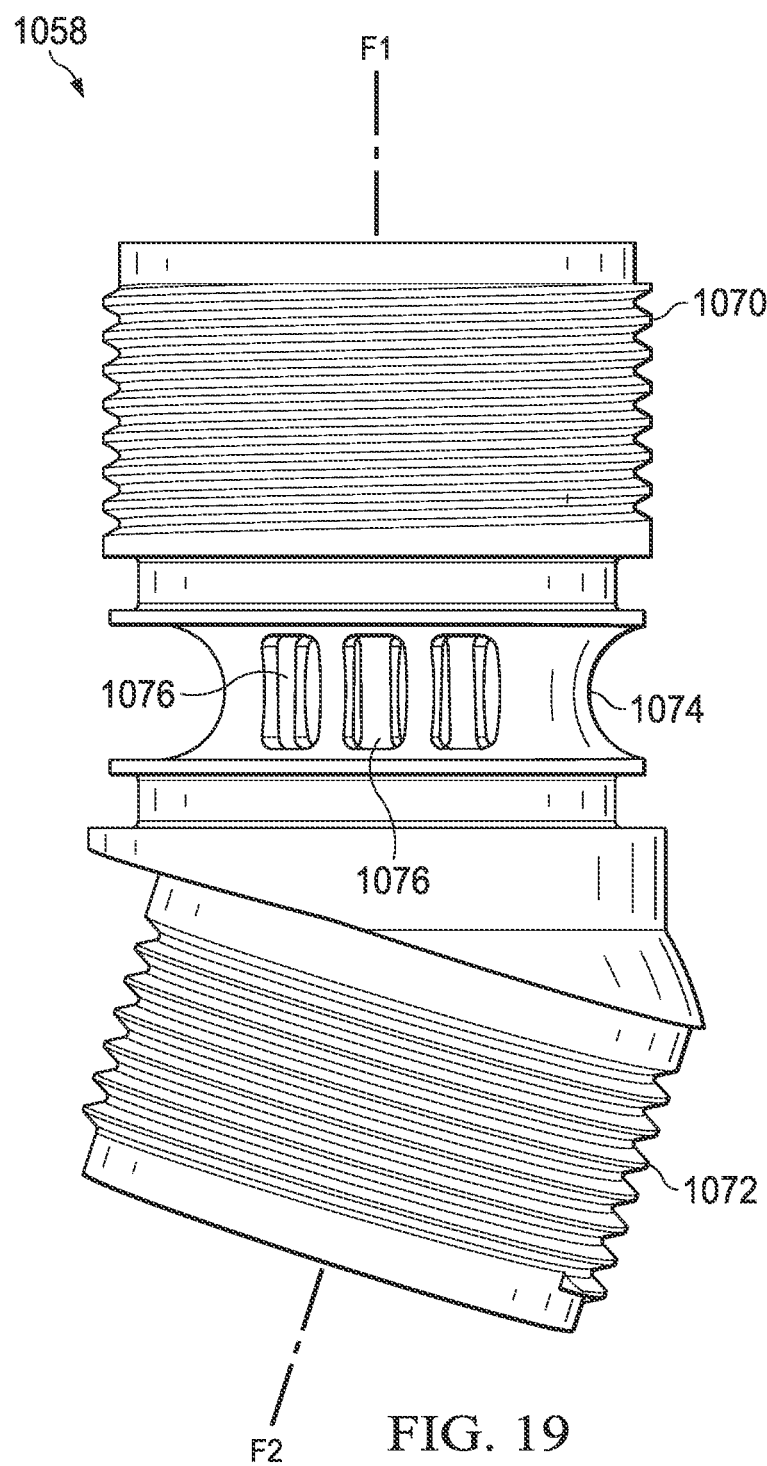

FIG. 19 illustrates a connector body of the connection member of FIG. 18A.

Figure 20:
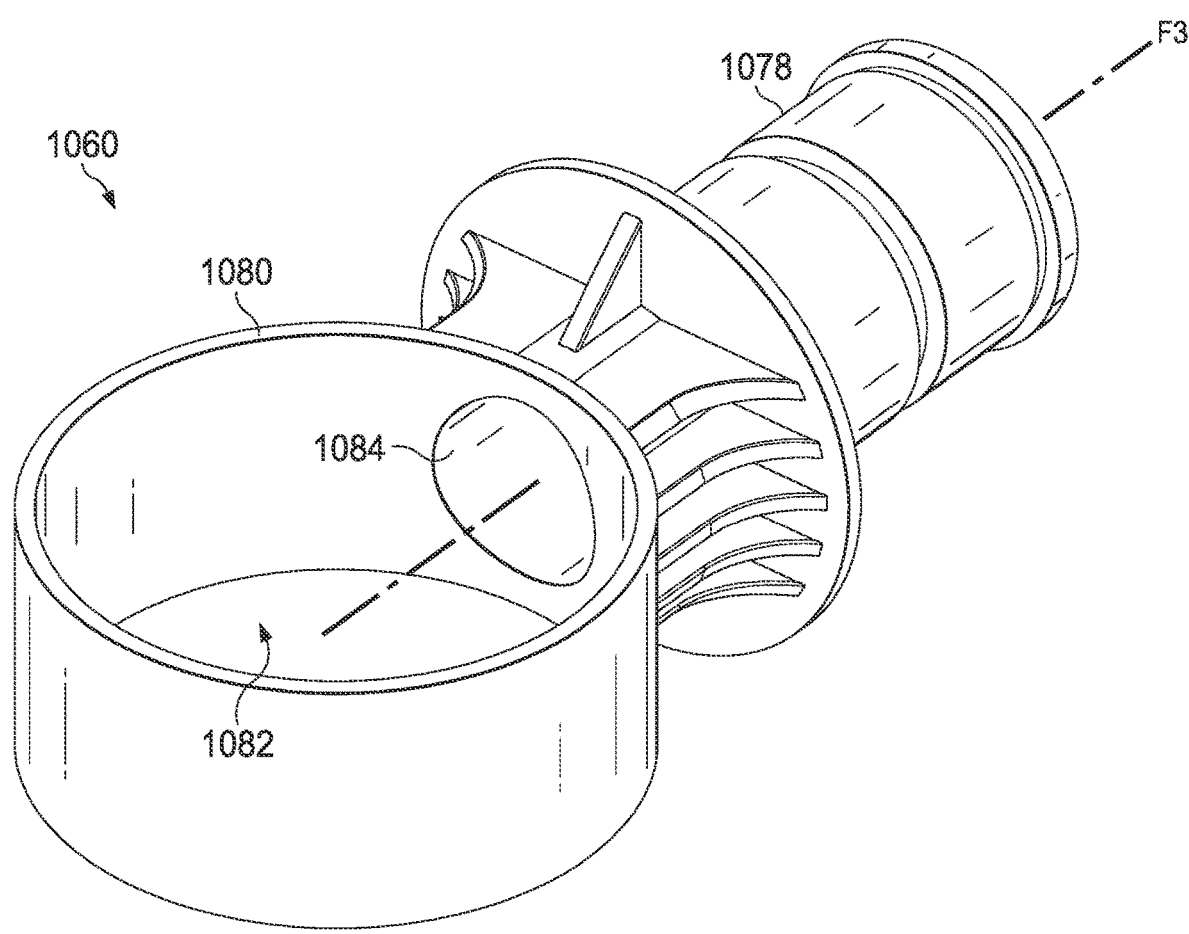

FIG. 20 illustrates a swivel port member of the connection member of FIG. 18A.

Figure 21:
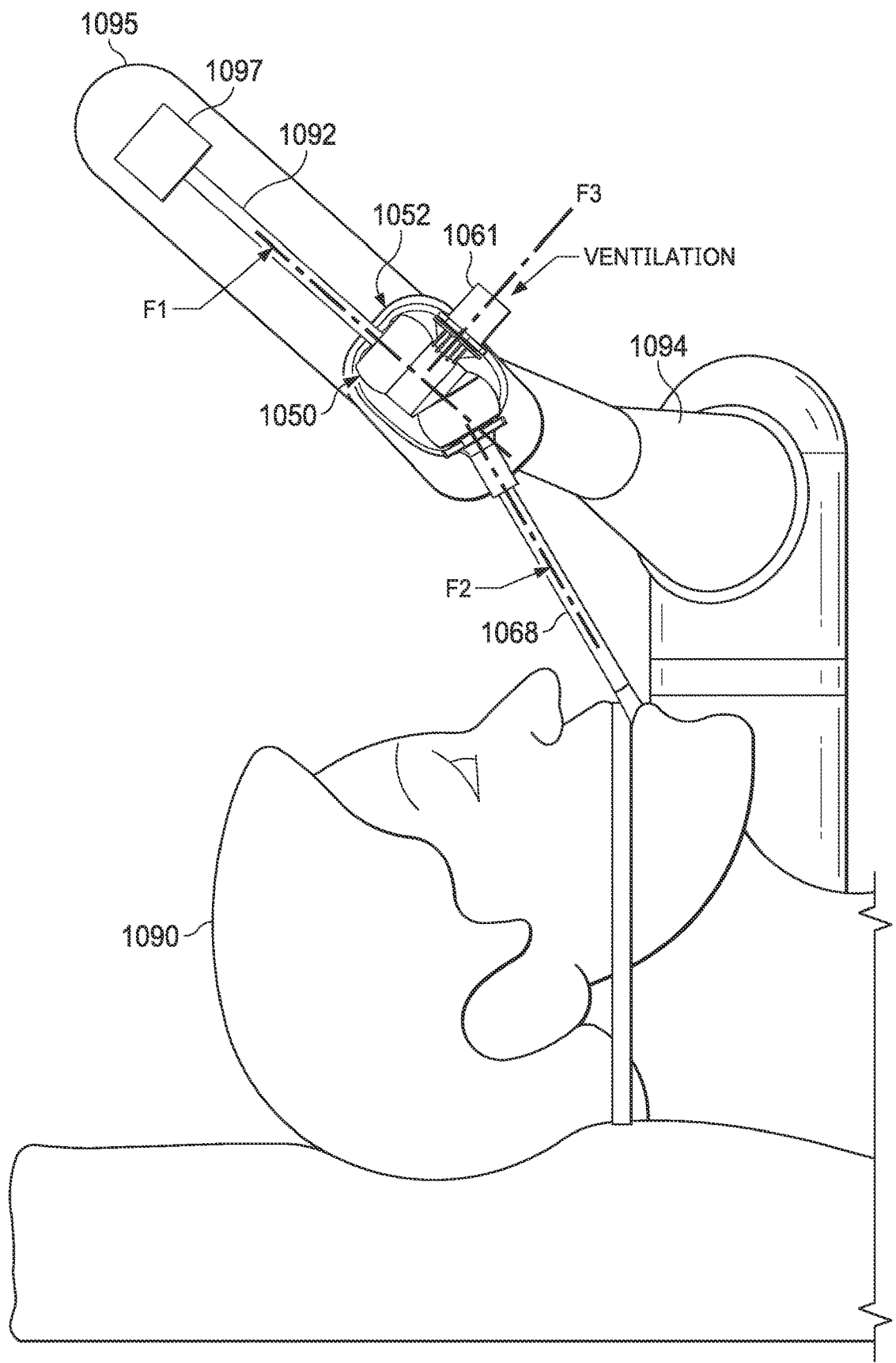

FIG. 21 illustrates a clinical environment in which the connection member of FIG. 18A may be used.

Figure 22:
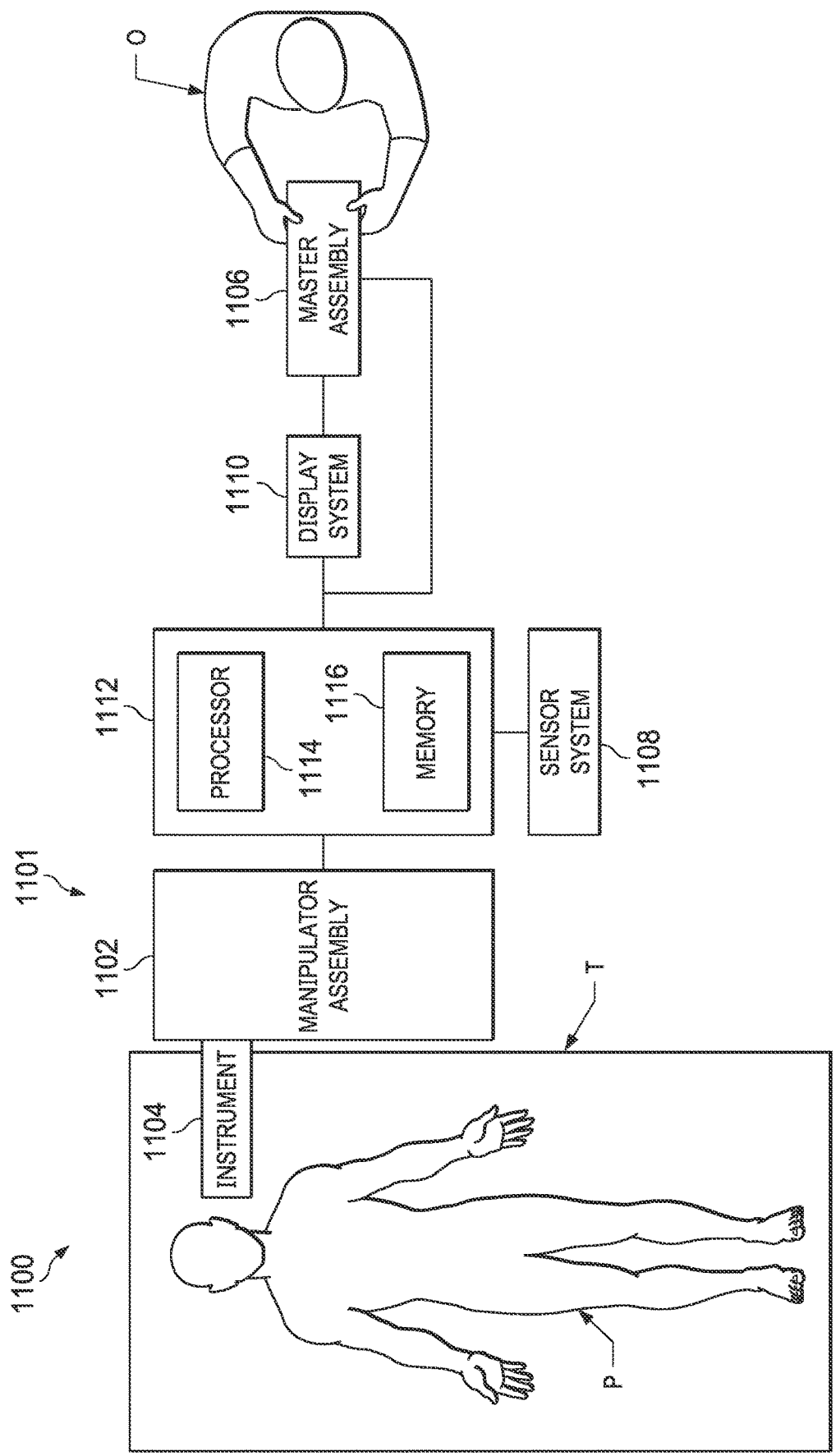

FIG. 22 is a simplified diagram of a medical system according to some examples.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The technology described herein provides connection between the anatomic orifice device and a robot-assisted medical system to promote patient safety during the medical procedure and to promote efficient coupling procedures.

Figure 1:
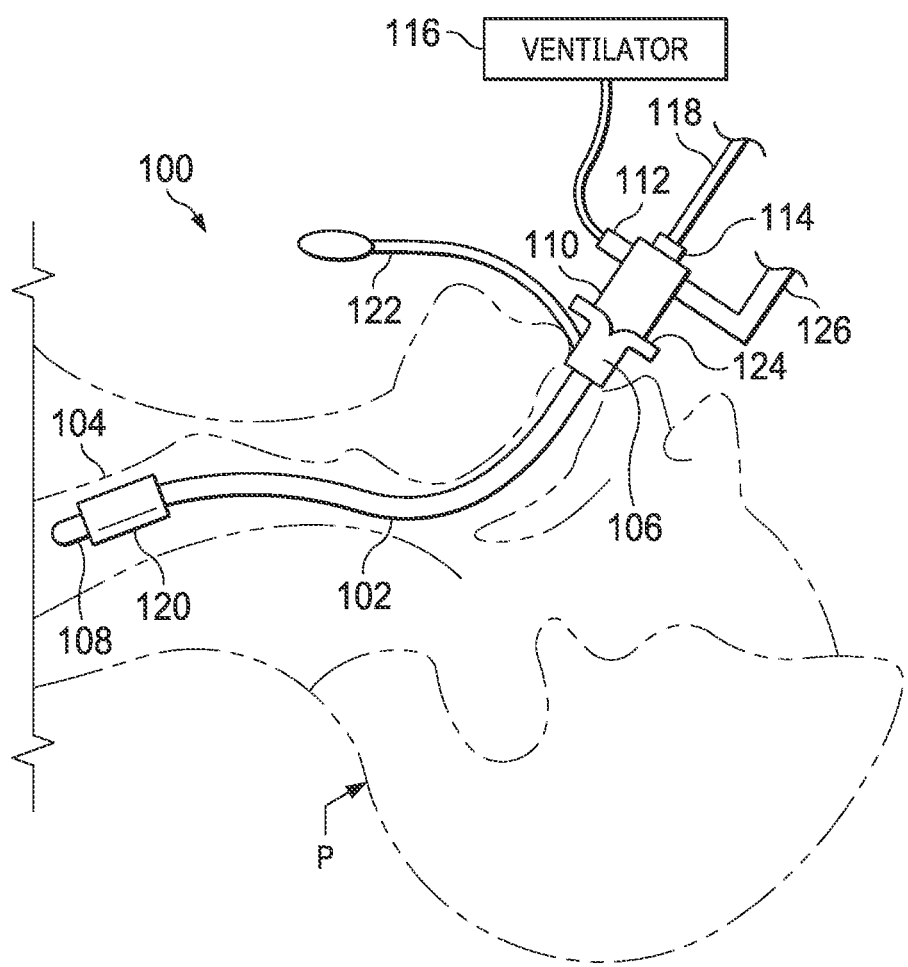
FIG. 1 illustrates an anatomic orifice device extending into a patient according to some examples.

FIG. 1 illustrates an example of an anatomic orifice device 100 inserted into the trachea 104 of a patient P through the patient's mouth while the patient lies on their back with the neck slightly extended. In some examples, the anatomic orifice device 100 may an endotracheal (ET) tube. An ET tube may be used for airway management, for example for use during mechanical ventilation as well for prevention of damage to patient anatomy such as vocal cords during the medical procedure. A laryngeal mask airway (LMA) may be used in place of an ET tube. Collectively, devices such as ET tubes and LMAs may be called airway management devices. Airway management devices may be one type of anatomic orifice device that provide entryway management and support of a natural or surgically created orifice in a patient anatomy. The anatomic orifice device 100 may comprise an elongated, flexible, and hollow tube 102 which may be curved between its proximal end 106 and its distal end 108 for insertion through the upper airway passages into the trachea 104. The proximal end 106 of the hollow tube 102 may be coupled to a connection member 110 which may include a ventilation port 112 an instrument port 114. The ventilation port 112 may be coupled to a ventilator device 116. The anatomic orifice device 100 provides a conduit to open the airway and to carry air into the patient's lungs. The ventilator device 116 may provide mechanical ventilation during the medical procedure, allowing the anatomic orifice device 100 to facilitate artificial ventilation when the patient P is unconscious or anesthetized during the medical procedure. A medical instrument 118 may then be fed through the instrument port 114 of the connection member 110, into the anatomic orifice device 100, and into the patient's airways to view the trachea and other bronchial passages, to diagnose lung diseases and infections, and/or to treat diseased or infected tissue.

The anatomic orifice device 100 may also include an inflatable balloon-like structure or cuff 120 disposed at the distal end 108 and inflatable using a cuff-inflating tube 122. This balloon-like structure or cuff 120 may seal the trachea and bronchial tree, thereby preventing air being pumped by the ventilator device 116 from escaping backward through the trachea 104 and entering the oral and nasal passages. As shown, anatomic orifice device 100 is placed within the trachea of the patient. In one example, the anatomic orifice device 100 may be mounted or constrained near the mouth of the patient by using a mount 124 attached to the tube 102.

Conventionally, the medical instruments that are used in surgical or other medical procedures are manually controlled by an operator. During the manual procedures, the operator handles the medical instruments, the bronchial instruments, and/or diagnostic instruments by introducing them through the airway management device to perform the medical procedure. As a result, the operator is able to sense and, therefore, control parameters (e.g., force, pressure, displacement, etc.) that affect movement of the medical instrument in relation to the patient anatomy during expected motions such as breathing and also during unexpected motions such as coughing. Thus, the operator can compensate for patient movement, preventing relative movement of the medical instrument and the airway management device. However, when the procedures are robot-assisted, anatomic orifice devices may be connected directly to a robot-assisted medical system and may be fixed and stationary relative to the robotic system in at least some degrees of freedom.

When the medical procedures are performed using medical instruments and a robot-assisted medical system, the connection member 110 may connect a manipulator assembly 126 of the robot-assisted medical system to the anatomic orifice device 100. Examples provided herein describe systems and methods for efficient coupling of the connection member with the robot-assisted medical system. To avoid trauma to the patient due to expected or unexpected patient motion during the medical procedure and/or to avoid dislodgement of the airway management device from the patient's trachea, various examples of connection members providing one or more degrees of freedom between the robot-assisted medical system and the anatomic orifice device 100 are described herein. In cases where the patient motion causes a significant amount of displacement, and therefore force on the connection member between the robot-assisted medical system and the anatomic orifice device 100, examples are provided herein for decoupling the connection member from either the robot-assisted medical system.

Figure 2A:
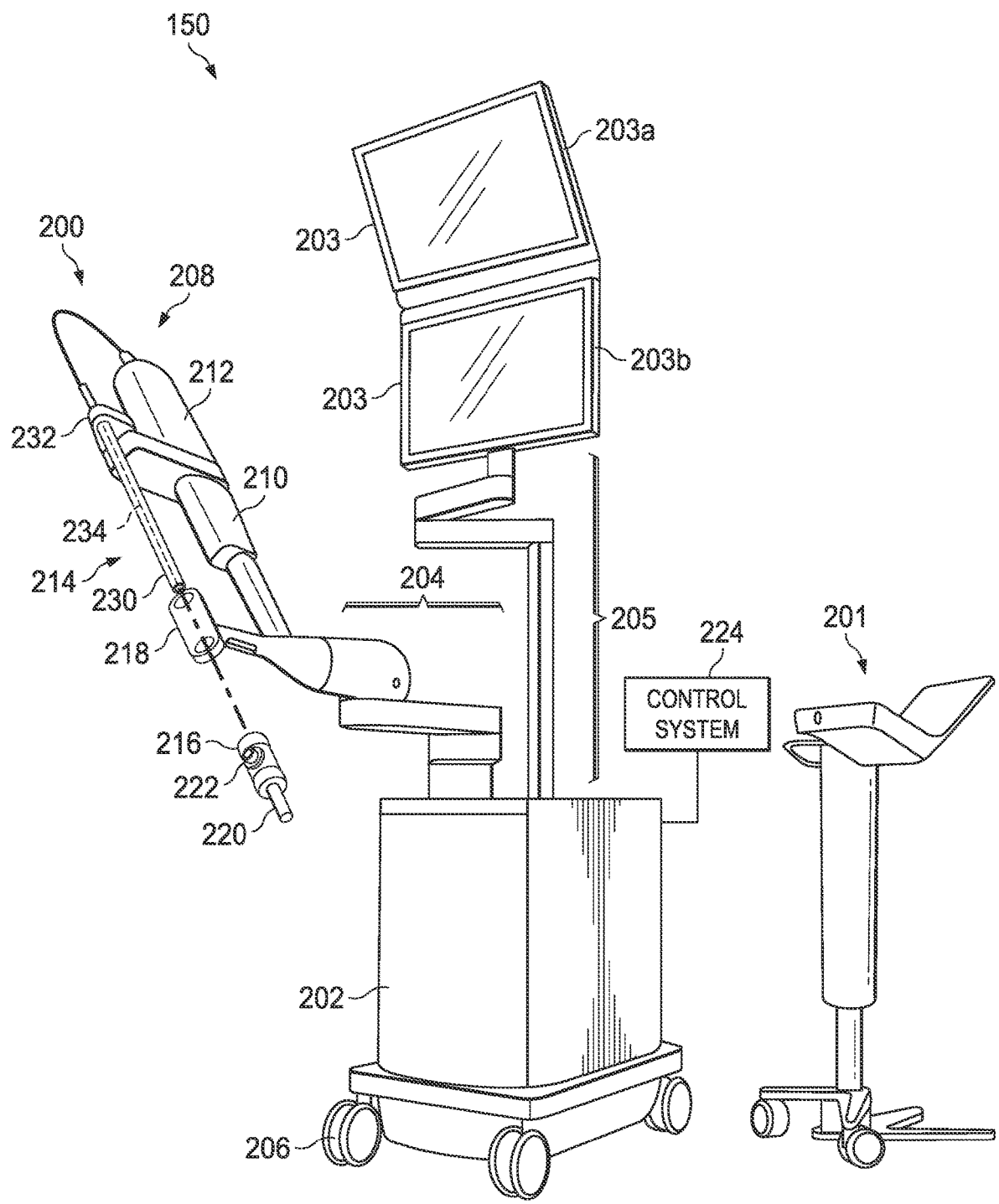
FIG. 2A illustrates a system including a manipulator assembly, a medical instrument, a connection member and an anatomic orifice device according to some examples.

FIG. 2A illustrates a medical system 150 including a master control 201 and a base 202 which supports a manipulator assembly 200 and a display system 203. The manipulator assembly 200 can be configured to support and position a medical instrument 214. Various elongate devices are described in PCT/US18/43041 (filed Jul. 20, 2018) (disclosing "Flexible elongate device systems and methods"), which is incorporated by reference herein in its entirety.

The base 202 is mounted on a set of wheels 206 to allow positioning of the base 202 at a desired location relative to the patient P. The base 202 also supports display system 203 which includes a support arm 205 and display monitors 203a, 203b. Support arm 205 includes multiple links and joints which provide adjustable positioning of display monitors 203a and 203b in the vertical and lateral directions, as well as rotationally about a vertical axis relative to the base 202, to position either monitor 203a, 203b at a desired viewing angle from the operator's point of view. The base 202 may also house various components including processors, monitors, vacuum equipment, air canisters, cables, etc. for performing various procedures on the patient P.

The master control 201 may include various input controls for an operator to use for interactively controlling operations of the manipulator assembly 200, for example functions performed by the manipulator assembly 200. In some examples, the master control 201 includes a scroll wheel and a trackball. In an example implementation, the scroll wheel may be rolled forwards or backwards in order to control the advancement or retraction of the medical instrument 214 with respect to the patient anatomy, and the trackball may be rolled in various directions by an operator in order to steer the position of the distal end portion and/or distal tip of the medical instrument 214, for example to control bend or articulation. Various systems and methods related to motion control consoles are described in PCT/US18/44419 (filed Jul. 30, 2018) (directed to "Systems and methods for safe operation of a device") and U.S. patent application Ser. No. 16/049,640 (filed Jul. 30, 2018) (disclosing "Systems and methods for steerable elongate device"), which are incorporated by reference herein in their entireties.

The manipulator assembly 200 may include an instrument manipulator 208 coupled to a support structure 204. The support structure 204 may be mounted to the base 202 and may include multiple coupled links that may be positioned by swiveling about joints, and extending, or retracting vertically, among other possible changes in direction and orientation, in order to place the instrument manipulator 208 at a working location and orientation. The links of support structure 204 may include non-servo controlled links (e.g., which may be manually positioned and locked into place) and/or one or more servo-controlled links (e.g., powered links that may be controlled in response to commands from a control system). In some embodiments, the links of the support structure 204 may be positioned using electronic circuitry and controls, including motors, to avoid manual intervention. In some embodiments, the links may be locked in place or unlocked to be manually manipulated by an operator interacting with switches, buttons, or other types of input devices as will be described in more detail below.

The instrument manipulator 208 may include an insertion stage 210 and an instrument carriage 212 to which the medical instrument 214 (e.g., medical instrument 118) is coupled. In this embodiment, medical instrument 214 includes an elongate device 230, such as a flexible catheter, coupled to an instrument body 232. The instrument carriage 212 may control insertion motion and/or motion of a distal end of the elongate device 230 in multiple directions including yaw, pitch, and roll. Instrument carriage 212 or insertion stage 210 may include actuators, such as servomotors that control motion of instrument carriage 212 along insertion stage 210.

The instrument 214 may include a shape sensor 234. Shape sensor 234 may include an optical fiber, extending within and aligned with elongate device 230, that forms a fiber optic bend sensor for determining the shape of the elongate device 230. In one alternative, optical fibers including Fiber Bragg Gratings (FBGs) are used to provide strain measurements in structures in one or more dimensions. Elongate device 230 may include a channel sized and shaped to receive a medical tool used for procedures such as surgery, biopsy, ablation, illumination, irrigation, or suction. Elongate device 230 may also house cables, linkages, or other steering controls.

A movable connection member 216 (e.g., connection member 110) is coupled to a mounting bracket 218 at a distal end of the insertion stage 210. The movable connection member 216 may support entry of the medical instrument 214 into an anatomic orifice device 220 (e.g., anatomic orifice device 100) and may also provide connection port 222 for the ventilator 116. To avoid trauma to the patient due to expected or unexpected patient motion during the medical procedure and/or to avoid dislodgement of the anatomic orifice device 220 from the patient's trachea, flexible and/or limited-movement connection members may be positioned between the robot-assisted medical system and anatomic orifice device. The connection member 216 is configured to move in various degrees of freedom to accommodate for the expected and unexpected patient motion. In cases where the patient motion causes a significant amount of displacement, and therefore force on the connection member 216, the connection member may decouple from either the manipulator assembly 200 or from the anatomic orifice device 220. The mechanisms for coupling and decoupling may be purely mechanical or may include sensors to sense the forces on the connection, and decouple, when necessary, the connection when the forces exceed a predetermined threshold to ensure patient safety. Alternatively, patient motion may be sensed using sensors coupled to the patient.

The anatomic orifice device 220 is inserted into the mouth and trachea of the patient P to help provide mechanical ventilation for the patient and to provide a conduit for the medical instrument 214 to be inserted into the lungs of the patient. While the medical instrument 214 is being navigated into the lungs to facilitate imaging, biopsy, and/or treatment, the patient may experience coughing, unexpected motion, or reduced sedation which may dislodge the endotracheal tube from the patient and disrupt ventilation. To minimize any consequences of this unexpected motion, the connection member 216 may be releasable from the mounting bracket 218.

The manipulator assembly 200 may be coupled to a controller or control system 224 of a robot-assisted medical system. Control system 224 may include at least one memory and at least one computer processor for effecting control of the manipulator assembly 200 and the medical instrument 214. Control system 224 may also include programmed instructions (e.g., a non-transitory machine-readable medium storing the instructions) to implement some or all of the methods described in accordance with aspects disclosed herein, including, for example, receiving sensor information, determining actions of the manipulator assembly based on sensor information, commanding operations of the manipulator assembly to move the mounting bracket, providing information to a display system, or performing other operations with the manipulator assembly, the medical instrument, or other systems connected to the control system.

Figure 2B:
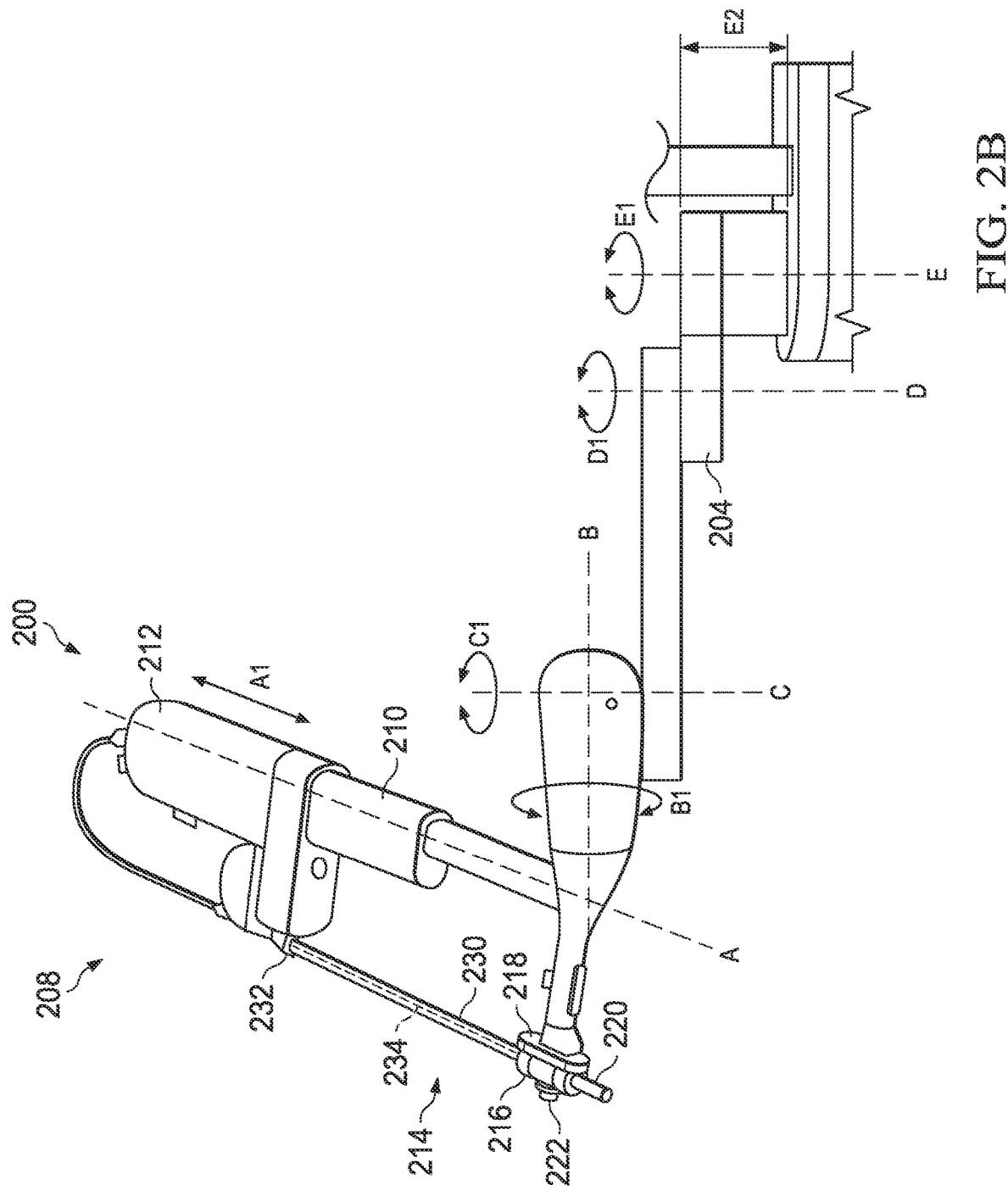
FIG. 2B illustrates a manipulator assembly including an instrument manipulator coupled to a support structure according to an embodiment of the present disclosure.

As shown in FIG. 2B, the instrument manipulator 208 according to various embodiments is configured to couple to medical instrument 214. Support structure 204 provides adjustments to position the instrument manipulator 208 and/or position medical instrument 214 at an optimal position and orientation relative to patient anatomy or other medical devices. For example, support structure 204 may provide for rotation E1 about axis E, extension/retraction E2 along axis E, rotation D1 about axis D, and rotation C1 about axis C, and rotation B1, about axis B, to position instrument manipulator 208 in a desired position relative to patient P. In some embodiments, optimal location and orientation can include alignment of the instrument manipulator 208 with respect to the patient anatomy, for example, for optimal positioning of the elongate device 230 to minimize friction within patient anatomy (e.g. anatomical openings, patient vasculature, patient endoluminal passageways, etc.) or within medical devices coupled to patient anatomy (e.g. cannulas, trocars, endotracheal tubes (ETT), laryngeal esophageal masks (LMA), etc.). In other embodiments, optimal location and orientation of the instrument manipulator 208 can additionally or alternatively include optimizing operator (e.g. operator O) ergonomics by providing sufficient operator workspace and/or ergonomic access to elongate device 230 when utilizing various medical tools such as needles, graspers, scalpels, grippers, ablation probes, visualization probes, and/or the like, with the elongate device 230.

Instrument manipulator 208 can be further configured to provide teleoperational, robot-assisted control, or other form of electronic controlled translation or manual translation A1 along axis A to provide for insertion and retraction of elongate device 230 with respect to patient anatomy. Each adjustment (e.g., A1, B1, C1, D1, E1, and E2) can be actuated by either robotic control or by manual intervention by an operator. For example, in one embodiment, each rotational or linear adjustment may be maintained in a stationary configuration using brakes such that depression of one or more buttons and switches releases one or more corresponding brakes allowing an operator to manually position the instrument manipulator. Additionally or alternatively, one or more adjustments may be controlled by one or more actuators (e.g., motors) such that an operator may use a button or switch to actuate a motor to alter the support structure 204 and/or the instrument manipulator 208 in a desired manner to position the manipulator assembly 200 in a desired configuration to provide an optimal position and orientation of the instrument manipulator 208.

Figure 3:
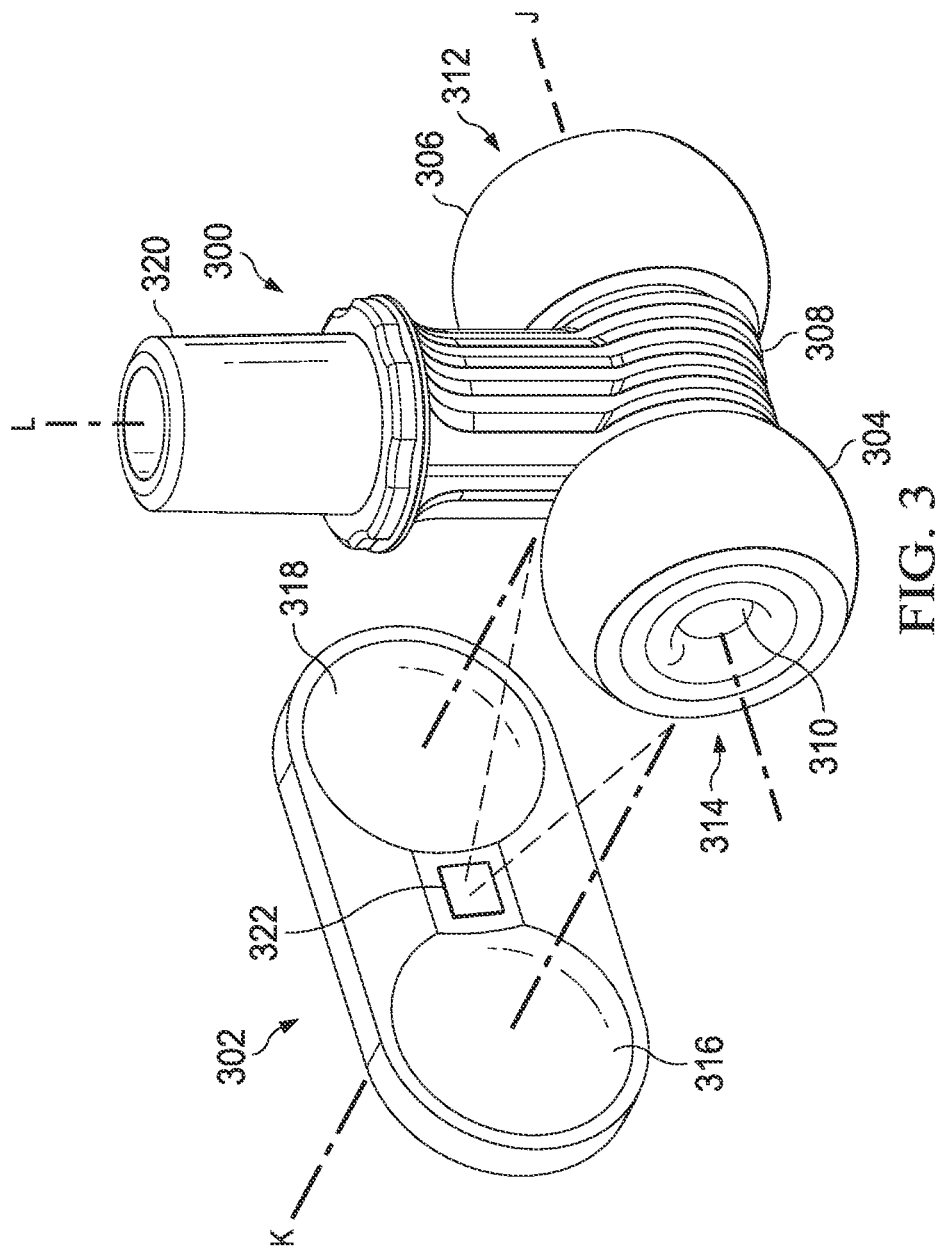
FIG. 3 illustrates a connection member and a guided mounting bracket according to some examples.

In some medical procedures, an anatomic orifice device may be placed into the patient anatomy and a connection member coupled to the anatomic orifice device before the mounting bracket is connected to the connection member. To avoid moving the patient, the manipulator assembly may move the mounting bracket into a position and/or orientation that allows the mounting bracket to be coupled to the connection member with minimal or no adjustment to the connection member orientation and/or position. FIG. 3 illustrates a connection member 300 and a mounting bracket 302. The connection member 300 may rotatably or swivelly couple to the mounting bracket 302 such that the connection member 300 rotates about an axis J relative to the mounting bracket 302. The mounting bracket 302 may be integrated into a manipulator assembly (e.g., manipulator assembly 126, 200) of a robot-assisted medical system. In some examples, the connection member 300 may be used as the connection member 216 and the mounting bracket 302 may be used as the mounting bracket 218. The connection member 300 may include cylindrical or toroidal-shaped coupling members 304 and 306 extending on opposite ends of a connector body 308. A passage 310 extends through the body 308. A first end 312 of the connection member 300 may receive an elongate device such as a medical instrument 214, and a second end 314 may couple to an anatomic orifice device such as anatomic orifice device 100, 220. The coupling members 304 and 306 mate with curved surfaces 316, 318, respectively, of the mounting bracket 302. The coupling members 304 and 306 may be retained magnetically, and accordingly, the members 304 and 306 and the mounting bracket 302 may include magnets and/or a material responsive to a magnetic field such as a ferromagnetic material. In some such examples, the mounting bracket 302 includes magnets, while the coupling members 304, 306 include magnets or a material responsive to a magnetic field, or vice-versa.

When magnetically attached, the coupling members 304 and 306 may rotate about the longitudinal axis J, with respect to the mounting bracket 302 and the manipulator assembly while the body 308 remains translationally coupled to the mounting bracket 302. The amount of rotation may be limited by contact with the mounting bracket 302, but in some examples a mounting bracket may permit a full 360° rotation. This rotation may occur in response to even slight movement of the patient or manipulator assembly. A port 320 may couple the connection member 300 to a source of air (e.g. ventilator device 116) and/or anesthesia. The magnetic connection may allow free rotation of the connection member 300 about axis J in response to forces from the air and anesthesia tubing. With the connection member 300 attached to an anatomic orifice device, larger patient movement may generate a force that causes the release of the coupling members 304 and 306 from the bracket 302. Thus, the connection member 300 coupled to the anatomic orifice device separates from the bracket 302. The magnets and magnetic material of the members 304, 306 and mounting bracket 302 may be selected to release in response to a predetermined force or motion but not release accidentally during minor motions associated with regular operation. The magnetic connections may be electromagnetic connections that may have a variable magnetic force at different stages of the procedure. For example, during installation, the magnetic force may be relatively low so that the user does not experience too great of a force as the connection mechanism approaches the docking spar. During the procedure, the magnetic force may be increased. In another example, if patient movement is detected using sensors, the magnetic force may be decreased to allow for disconnect. In some embodiments, the portions of the connection member 300 that couple to the air source, the medical instrument, and/or the anatomic orifice device rotate or permit rotation relative to the connection member 300 to make the connections more compliant and to make it easier to complete the connections. This may also prevent the coupled devices from inadvertently causing the connection member 300 to release from the mounting bracket 302 or from inadvertently preventing the connection member 300 from releasing.

In the example of FIG. 3, a guided mounting system may include a sensor system 322 that tracks the connection member 300 and communicates with a control system (e.g., control system 224) of a robot-assisted medical system to move the mounting bracket 302, and/or the manipulator assembly to which the mounting bracket is coupled, into a position and orientation for coupling to the connection member 300. The sensor system 322 (or portions thereof) may be incorporated into the mounting bracket 302, into the manipulator assembly, into another component of a robot-assisted medical system, into the connection member 300, or into another component in the patient environment. In some examples, the sensor system 322 senses a spatial relationship, including a position and orientation offset, between the mounting bracket 302 and the connection member 300. The control system may receive an indication of the spatial relationship from the sensor system 322 and determine a mounting configuration for the mounting bracket 302. The mounting configuration may include a position and orientation of the mounting bracket 302 for mating with the connection member 300. The control system may command the movement of the mounting bracket 302 into the determined mounting configuration. In this example, the mounting bracket 302 may move from a fully separated configuration into full, mounted contact with the connection member 300 based on controlled motion of the mounting bracket 302. In some embodiments, the commanded movement of the mounting bracket 302 will include correction of the rotational alignment and elevation of the mounting bracket 302 to match the orientation and elevation of the connection member 300. This automatic elevation and rotational alignment may be accomplished with the sensor system 322 calibrated to the action of the manipulator arm to which the mounting bracket 302 is connected.

The sensor system 322 may include one or more technologies that may be used to identify and determine the position and orientation of the connection member 300 relative to the mounting bracket 302 when the connection member 300 is within a proximity threshold to the mounting bracket 302. These technologies may signal the control system to drive motors that move the position and orientation of the mounting bracket 302 to connect the mounting bracket 302 to the connection member 300.

For example, the sensor system 322 may comprise an optical sensor which may include a paired infrared emitter and infrared sensor, a paired laser emitter and laser sensor, imaging devices, or any other type of light-based sensors. In some examples, the sensor system 322 may include an electromagnetic proximity sensor including a paired electromagnetic emitter and receiver, a paired radio transmitter and receiver, one or more radio transceivers, a magnetic field sensor, an acoustic (e.g., ultrasonic) sensor, a position sensor, and/or a force sensor. The sensor system 322 may sense distance, velocity, acceleration, orientation, force, or other factors associated with the spatial relationship between the connection member 300 and the mounting bracket 302. In some examples, the sensor system 322 may sense a detectable feature of the connection member 300 such as a magnetic field generated by magnets in the coupling members 304, 306. In other examples, the detectable feature may include, for example, a shape of the connection member 300, optical signature, electromagnetic feedback, acoustic signature, a marker on the connection member, a radio transmitter on the connection member, a near field communication chip on the connection member, a radio-frequency identification chip on the connection member, movement and/or application of force to a member in contact with the connector member 300, etc.

In some examples of a sensor system 322, position and orientation may be determined using a computer vision system including two or more cameras for use in object detection, object recognition and/or distance measurement systems. As another example, position and orientation may be determined using two or more electromagnetic sensors (e.g., infrared (IR), laser) that generate and emit an electromagnetic field or beam of electromagnetic radiation and that receive and measure changes and differences in the returned electromagnetic signals. As another example, position and orientation may be determined using one or more magnetic field sensors that measure the change in the magnetic field when the connection member 300, with magnets and/or materials responsive to a magnetic field, approaches the mounting bracket 302. As another example, one or more of distance, velocity, acceleration, and/or force sensors may be used to determine position and orientation once the connection member 300 has made initial, partial or full contact with the mounting bracket 302. Signals generated from these sensors may be supplied to the control system to drive motors that move the position and orientation of the mounting bracket 302 relative to the connection member 300. In some embodiments, the sensor system 322 may cooperate with a sensor component of the connection member to determine the position and orientation of the connection member 300 relative to the mounting bracket 302. For example, the sensor system 322 may include a radio transmitter and the sensor component of the connection member 300 may include a radio receiver (or vice versa), or the sensor system 322 may include an electromagnetic field generator and the sensor component of the connection member 300 may include an electromagnetic field receiver (or vice versa).

In some examples, the sensor system 322 may include one or more wireless technologies, including near field communication (NFC), radio-frequency identification (RFID), and/or Bluetooth, which may be used to determine whether the connection member 300 is within a proximity threshold to the mounting bracket 302.

Figure 4A:
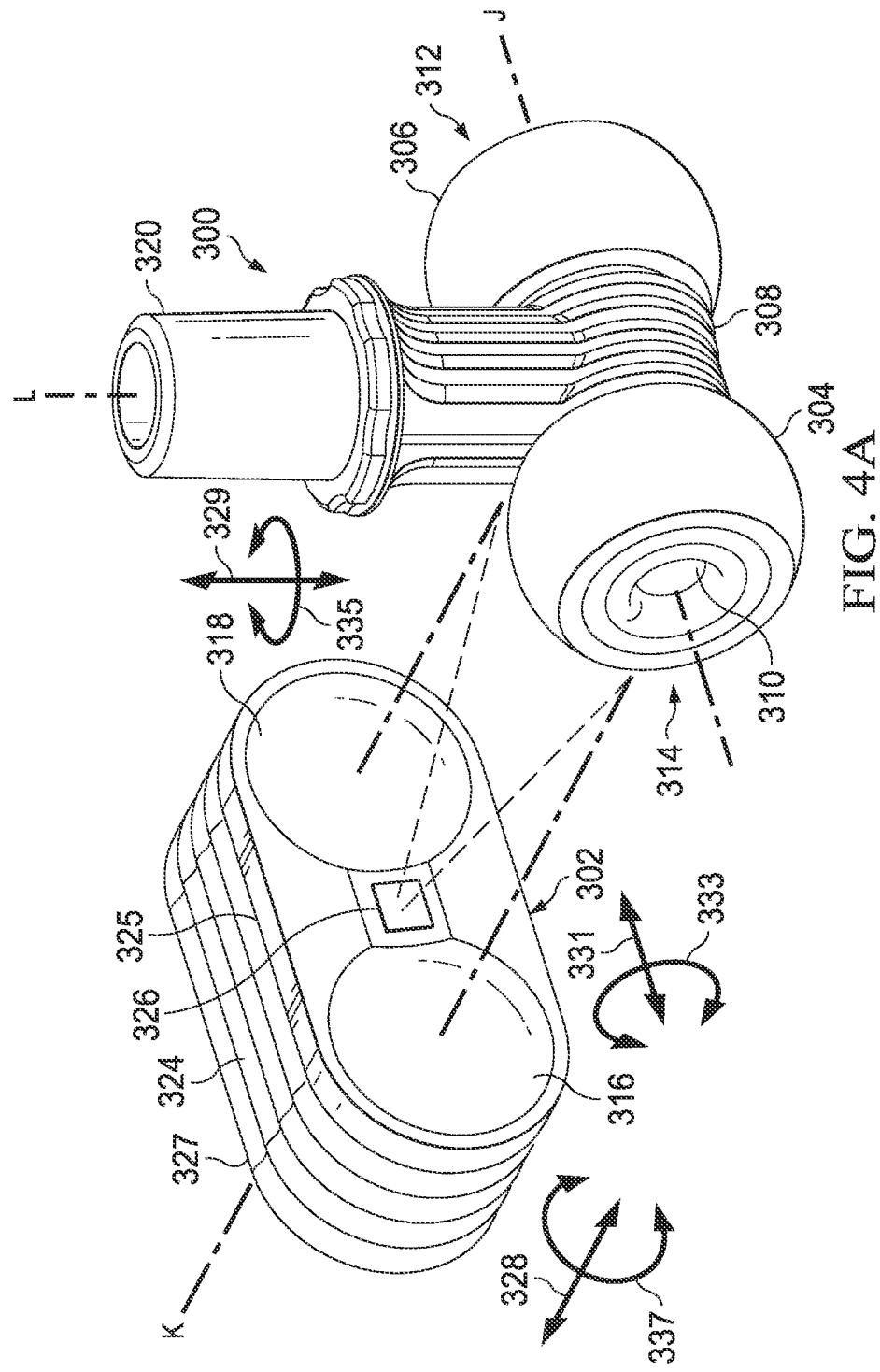
FIGS. 4A-4C illustrates a connection member and a guided mounting bracket with a flexible connector according to some examples.

FIG. 4A illustrates the connection member 300 and mounting bracket 302. In this example, a flexible connector 324 includes a distal end 325 and a proximal end 327. The proximal end 327 may be coupled to a manipulator assembly (e.g., manipulator assembly 200). The distal end 325 may be coupled to the mounting bracket 302 such that the flexible connector 324 extends between the mounting bracket 302 and the manipulator assembly. The flexible connector 324 may be, for example, a bellows or a spring that may extend, stretch, and flex, allowing the mounting bracket 302 to move into limited or close contact with connection member 300 and may bias the mounting bracket 302 into a retracted position close to the manipulator assembly. For example, the distal end 325 and mounting bracket 302 may extend and/or retract relative to the proximal end 327 as shown by arrow 328. Further, the distal end 325 and mounting bracket 302 may move up and/or down relative to the proximal end 327 as shown by arrow 329. Further, the distal end 325 and mounting bracket 302 may move left and/or right relative to the proximal end 327 as shown by arrow 331. Further, the distal end 325 and mounting bracket 302 may rotate in a yaw direction (generally about an axis parallel to the arrow 329) relative to the proximal end 327 as shown by arrow 335. Further, the distal end 325 and mounting bracket 302 may rotate in a pitch direction (generally about an axis parallel to the arrow 331) relative to the proximal end 327 as shown by arrow 333. Further, the distal end 325 and mounting bracket 302 may rotate in a roll direction (generally about an axis parallel to the arrow 328) relative to the proximal end 327 as shown by arrow 337.

With the flexible connector 324 extended, stretched, or flexed, the mounting bracket 302 may be in limited or close contact with the connection member 300 achieved for example, by manual movement of the mounting bracket 302, magnetic attraction between the mounting bracket 302 and the connection member 300, or commanded motion from a control system. In some examples, the mounting bracket 302 may be manually aligned and connected with the connection member 300. For example, the curved surface 316 of mounting bracket 302 may be brought in contact with the coupling member 304 of connection member 300, and the curved surface 318 of mounting bracket 302 may be brought in contact with the coupling member 306 of connection member 300. The mounting bracket 302 may be magnetically held in contact and alignment with connection member 300. While the mounting bracket 302 and connection member 300 are in contact and alignment, the proximal end 327 of the flexible connector 324 might not be aligned with the distal end 325 or with the mounting bracket 302 (and consequently not aligned with the connection member 300). The control system may detect the misalignment between the proximal end 327 of the flexible connector 324 and the mounting bracket 302 and may bring the proximal end 327 in alignment with the mounting bracket 302 and connection member 300 by driving motors that move the position and orientation of the manipulator assembly that is coupled to the proximal end 327 of the flexible connector 324. Additionally or alternatively, the manipulator assembly may be manually moved by an operator to bring the proximal end 327 in alignment with the mounting bracket 302 and connection member 300.

Figure 4B:
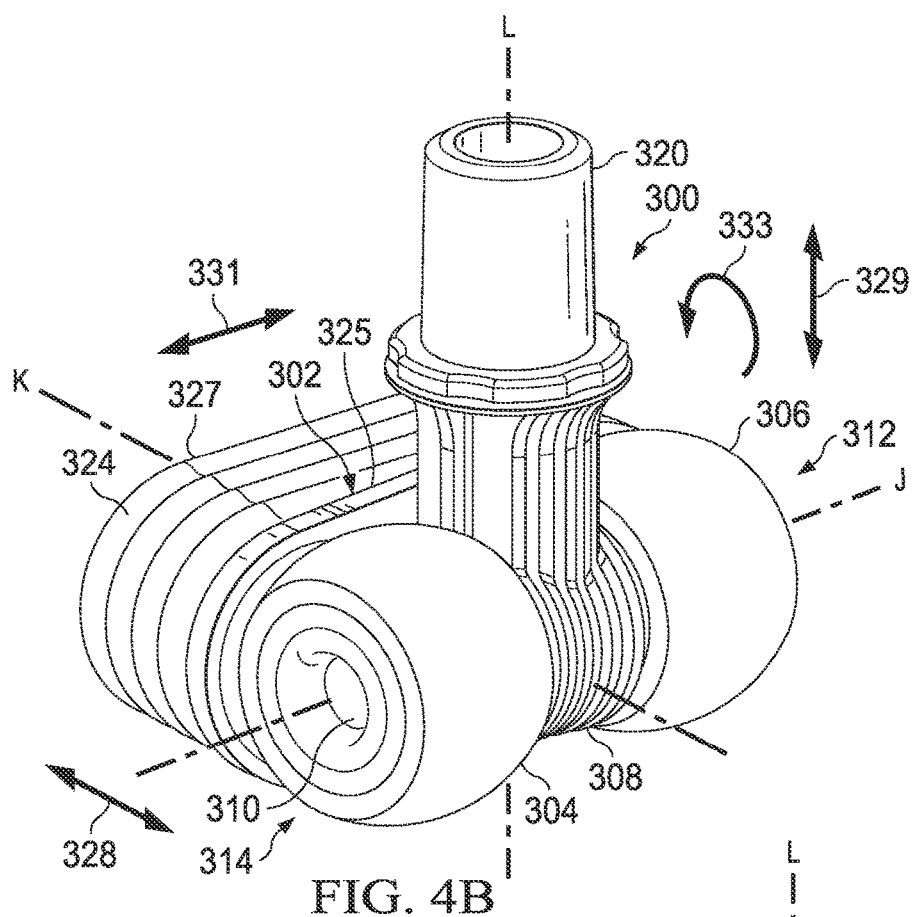
Figure 4C:
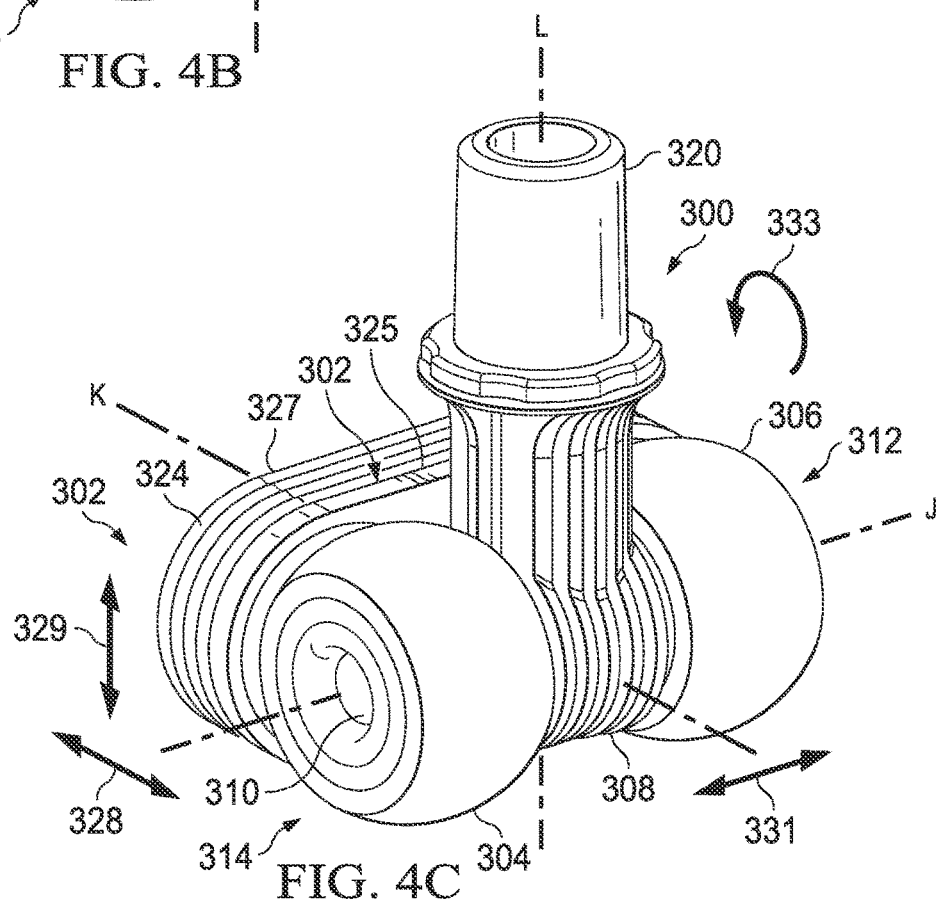

In the example of FIG. 4A, a guided mounting system may include a sensor system 326 that may be located within the mounting bracket 302, within the flexible connector 324, or within the manipulator assembly. The sensor 326 may detect when the connection member 300 is in close, partial, limited, and/or light contact with the mounting bracket 302. The sensor 326 may communicate with a control system of a robot-assisted medical system to move the manipulator in or more degrees of freedom to move the mounting bracket 302 near or into contact with the connection member 300. Additionally or alternatively, the mounting bracket 302 may be manually moved to contact the connection member 300. Magnetic attraction between the mounting bracket 302 and the connection member 300 may cause the coupling members 304, 306 to engage the surfaces 316, 318, respectively. At least initially, the engagement may occur in a non-aligned configuration with the distal end 325 of the flexible connector 324 and the mounting bracket 302 extended away from (e.g., stretched) and/or skewed with respect to the proximal end 327 of the flexible connector 324, as shown in FIG. 4B. After this initial engagement in which the proximal end 327 and the distal end 325 of the flexible connector are out of alignment, one or more degrees of freedom of the manipulator assembly may be adjusted to bring the proximal end 327 of the flexible connector 324 into alignment with the distal end 325 of the flexible connector 324, as shown in FIG. 4C, to create a secure mount between the mounting bracket 302 and the connection member 300.

In some examples, the sensor 326 may sense a distance, velocity, acceleration, orientation, force, or other factors associated with the spatial relationship between the connection member 300 and the mounting bracket 302. The sensor 326 may include one or more non-contact sensors including magnetic, electromagnetic, optical, photoelectric, and/or acoustic sensors that detect the connection member 300 spaced apart from the mounting bracket 302. The sensitivity of the spatial relationship sensor may be determined, for example, by the power of the emitter and/or the sensor capacity. A control system (e.g., control system 224) may receive an indication of the spatial relationship from the sensor 326 and determine a full mounting configuration for the mounting bracket 302. The control system may command the movement of the support structure 204 and/or mounting bracket 302 into the determined mounting configuration to achieve a full mating contact with the connection member 300. In this example, the mounting bracket 302 may move from a spaced apart position within a predetermined distance from the connection member 300, a partial contact position with the connection member 300, a limited contact position with the connection member, or a light contact position in which the mounting bracket is not fully mounted with the connection member 300 into a fully mounted configuration based on controlled motion of the mounting bracket 302. The full mounting configuration may include a position and orientation of the mounting bracket 302 for full mating contact and orientation alignment with the connection member 300. When the mounting bracket 302 is in the full mounting configuration, the flexible connector 324 may be stretched and/or skewed as shown in FIG. 4B or the proximal end 327 of the flexible connector 324 may be aligned with the distal end 325 of the flexible connector 324 as shown in FIG. 4B. In some examples, when the connection member 300 is in a fully mounted configuration, the flexible connector 324 may be in a fully retracted, unflexed state. In other examples, the connection member 300 may be in a fully mounted configuration with the mounting bracket 302 while the flexible connector 324 is at least partially stretched or flexed. During a medical procedure, the mounting bracket 302 may remain in the fully mounted configuration even as the distal end 325 of the flexible connector 324 and the mounting bracket 302 move slightly with respect to the proximal end 327 of the flexible connector 324 and the manipulator assembly due to acceptable patient movements such as respiration. The flexibility of the flexible connector 324 and the strength of the magnetic attraction may be chosen to ensure that the connection member 300 decouples from the mounting bracket 302 if the movement of the patient relative to the manipulator assembly exceeds a predetermined threshold.

FIGS. 5A and 5B schematically illustrate a connection member 400 for coupling with a mounting bracket 402. In some examples, the connection member 400 may be used as the connection member 216 and the mounting bracket 402 may be used as the mounting bracket 218. The connection member 400 may include coupling members 420, 422 attached to a connector body 424 and may be similar to connection member 300. In this example the coupling members 420, 422 may have a cylindrical or toroidal shape with a diameter smaller than a diameter of the connector body 424. In alternative embodiments, the coupling members may have a larger diameter than the connector body, as in connection member 300. The coupling members 420, 422 may include a magnet or material responsive to a magnetic field, such as a ferromagnetic material. In some examples, the connector body 424 may be formed of plastic or another material that is non-responsive to a magnetic field.

In this example, the mounting bracket 402 includes a mounting housing 404 and a movable mounting component 406 that is movable relative to the mounting housing 404. The movable mounting component 406 may include a receiving platform 408 and a biasing member 410 such as a spring. The receiving platform 408 may have curved surface 409 shaped to mate with the connector body 424. The movable mounting component 406 is positioned in the housing 404 between fixed mounting components 412, 414. The fixed mounting components 412, 414 may be fixed positionally and rotationally relative to the housing 404. The fixed mounting components 412, 414 may include magnets 416 and may have curved surfaces 418, 419 shaped to receive the coupling members 420, 422, respectively.

As shown in FIG. 5A, the receiving platform 408, biased by the biasing member 410, may be extended outward from the fixed mounting components 412, 414 as the mounting bracket 402 is moved into proximity of the connection member 400. The connector body 424 may contact the receiving platform 408 while the receiving platform 408 is extended outward from the fixed mounting components 412, 414. With the connector body 424 in the proximity of or in contact with the raised receiving platform 408, the connection member 400 may rotate about the axis L until the magnets 416 have aligned the connection member 400 and the coupling members 420, 422 in a predetermined rotational configuration. The connector body 424 may rotate with respect to the receiving platform 408 as the connection member 400 rotates about the axis J. As illustrated in FIG. 5B, the coupling members 420, 422 may contact the surfaces 418, 419, respectively, and may be magnetically retained in the predetermined rotational configuration by the magnets 416. When the coupling members 420, 422 are drawn to and in contact with the surfaces 418, 419, the receiving platform 408 may be pushed into the housing 404 and recessed relative to the fixed mounting components 412, 414. In some embodiments, the magnets 416 may be electromagnets with power and polarity controlled by a control mechanism 428 (which may be part of the control system 224). The control mechanism 428 may be connected to a sensor system 426 that detects when the connection member 400 and the coupling members 420,422 are located and oriented in the predetermined rotational configuration. In this example, the control mechanism 428 may activate the magnets 416. The sensor system 426 may include an optical sensor, a force sensor, a position sensor, a velocity sensor, an accelerometer or other types of sensors for monitoring the engagement of the connection member 400 with the mounting bracket 402. In some examples, the control mechanism 428 can deactivate the magnets 416, causing the biased mounting component 406 to push outward and eject the connection member 400 from connection with the mounting bracket 402.

FIGS. 6A and 6B schematically illustrate a connection member 450 for coupling with a mounting bracket 452. In some examples, the connection member 450 may be used as the connection member 216 and the mounting bracket 452 may be used as the mounting bracket 218. The connection member 450 may include coupling members 470, 472 attached to a connector body 474. In this example the coupling members 470, 472 may have a cylindrical or toroidal shape with a diameter smaller than a diameter of the connector body 474. In this example, the coupling members 470, 472 may be made of plastic or another material that is non-responsive to a magnetic field. The connector body 474 may include a magnet or material responsive to a magnetic field, such as a ferromagnetic material.

In this example, the mounting bracket 452 includes a mounting housing 454 and a central, fixed mounting component 456 that is stationary relative to the mounting housing 454. The fixed mounting component may include a magnet 466 and a curved receiving platform 458 shaped to mate with the connector body 474. The fixed mounting component 456 is positioned in the housing 454 between movable mounting components 462, 464. The movable mounting components 462, 464 may include receiving platforms 468, 469, respectively, and biasing members 460, 461, respectively. The biasing members 460, 461 may include springs.

As shown in FIG. 6A, the receiving platforms 468, 469 biased by the biasing member 460, 461, may be extended outward from the fixed mounting component 456 as the mounting bracket 452 is moved into proximity of the connection member 450. The coupling members 470, 472 may contact the receiving platforms 468, 469, respectively, while the receiving platforms are extended outward from the fixed mounting component 456. With the coupling members 470, 472 in the proximity of or in contact with the raised receiving platforms 468, 469, the connection member 450 may rotate about the axis L until the magnet 466 has aligned the connection member 450 and the coupling members 470, 472 in a predetermined rotational configuration. The coupling member 470 may rotate with respect to the receiving platform 468 and the coupling member 472 may rotate with respect to the receiving platform 469 as the connection member 450 rotates about the axis J. As illustrated in FIG. 6B, the connector body 474 may contact the receiving platform 458 and may be magnetically retained in the predetermined rotational configuration by the magnet 466. When the connector body 474 is drawn to and in contact with the receiving platform 458, the receiving platforms 468, 469 may be pushed inward into the housing 454. In some embodiments, the magnet 466 may be an electromagnet with power and polarity controlled by a control mechanism 478 (which may be part of the control system 224). A sensor system 476 may include an optical sensor, a pressure sensor, a velocity sensor or other types of sensors for monitoring the engagement of the connection member 450 with the mounting bracket 452. In some examples, the control mechanism 478 can deactivate the magnet 466, causing the biased mounting components 462, 464 to push outward and eject the connection member 450 from connection with the mounting bracket 452.

Figure 7:
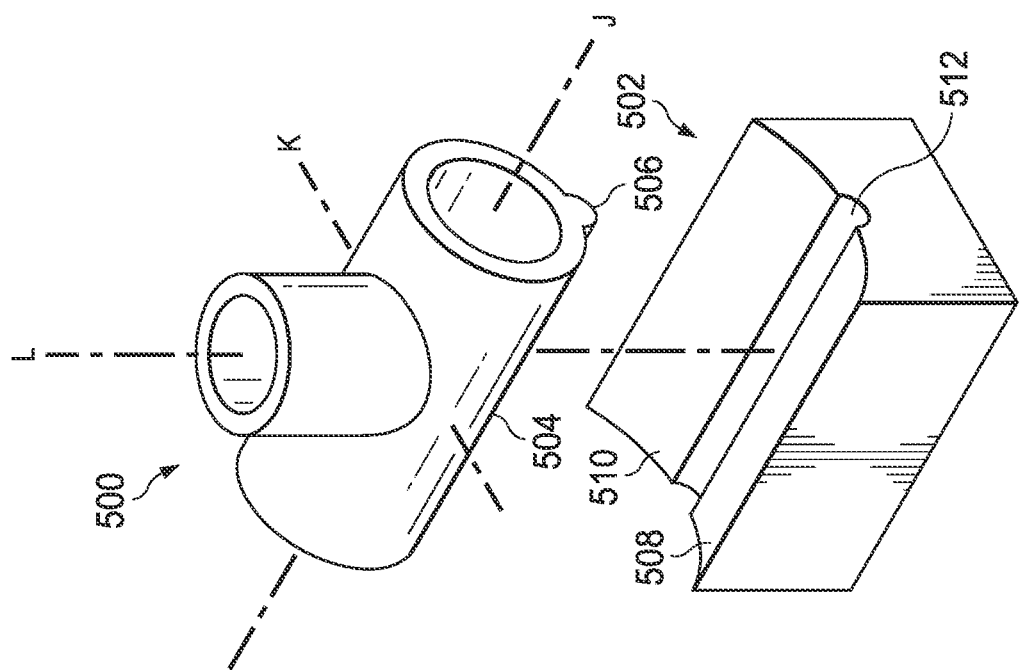
FIG. 7 illustrates a connection member and a mounting bracket with wing extensions according to some examples.

FIG. 7 is a perspective view of a connection member 500 for coupling with a mounting bracket 502. In some examples, the connection member 500 may be used as the connection member 216 and the mounting bracket 502 may be used as the mounting bracket 218. In this example, the mounting bracket 502 has a large surface to capture and direct an orientation of the connection member 500 as the mounting bracket 502 is moved into connection with the connection member 500. In various embodiments, the connection member 500 may include any configuration of connection member and connector body/coupling mechanism configurations described herein. The connection member 500 may include a connector body 504 and an elongated projection 506 extending along an outer surface of the connector body 504. The elongated projection may extend generally parallel to an axis of rotation J of the connector body 504. In this example, the mounting bracket 502 includes a wing extension 508 and a wing extension 510 between which extends an elongated groove 512. The wing extensions 508, 510 may have curved or flat surfaces. As the mounting bracket 502 is moved toward the connection member 500, the wing extensions 508, 510 may passively catch the connection member 500 and adjust it about any of the axes J, K, L, to align the connection member 500 with the mounting bracket 502. The wing extension 508, 510 may urge the elongated projection 506 into the groove 512 as the mounting bracket 502 moves closer to the connection member 500. With the elongated projection 506 positioned in the groove 512, the connection member 500 may be fully mounted in an operational position and configuration to the mounting bracket 502.

Figure 8:
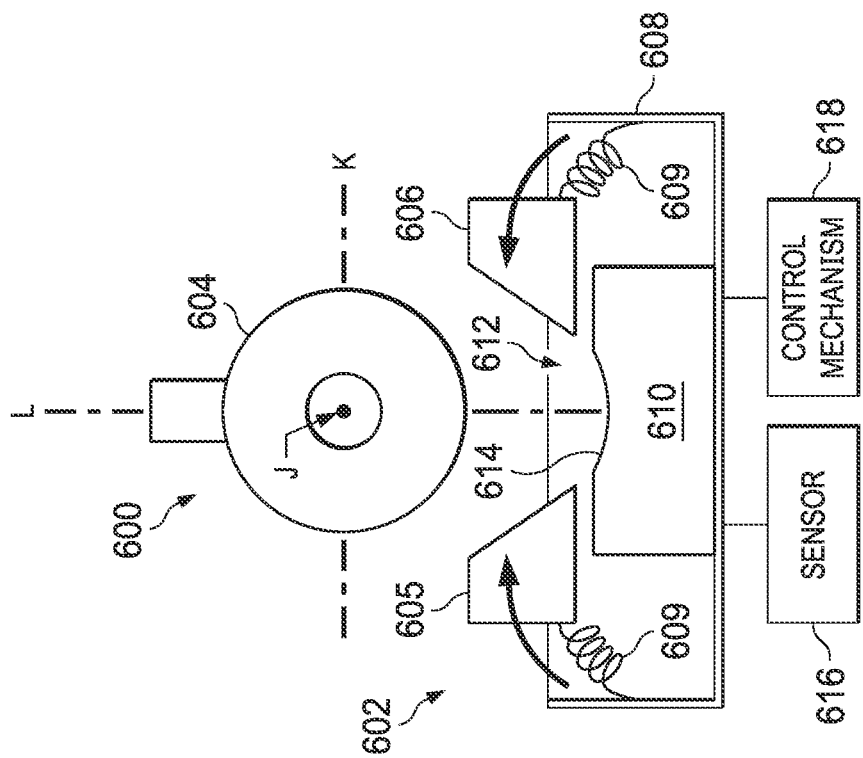
FIG. 8 illustrates a connection member and a mounting bracket with wing extensions according to some examples.

FIG. 8 is a schematic view of a connection member 600 for coupling with a mounting bracket 602. In some examples, the connection member 600 may be used as the connection member 216 and the mounting bracket 602 may be used as the mounting bracket 218. In this example, the mounting bracket 602 has a set of retractable wing extensions 605, 606 to capture and direct an orientation of the connection member 600 as the mounting bracket 602 is moved into connection with the connection member 600. The connection member 600 may include a connector body 604. In various embodiments, the connection member 600 may include any configuration connection member and connector body/coupling mechanism configurations described herein. In this example, mounting bracket 602 may include a housing 608, and the retractable wing extensions 605, 606 may move relative to the housing 608. A base platform 610 may span a gap 612 between the wing extensions 605, 606. The base platform 610 may include an elongated curved receiving surface 614 that is shaped to mate with a curve of the connector body 604. While not shown in FIG. 8, the receiving surface 614 may include an elongated groove (e.g., the elongated groove 512 shown in FIG. 7), and the connector body 604 may include a corresponding elongated projection (e.g., the elongated projection 506 shown in FIG. 7). The wing extensions 605, 606 may have curved or flat surfaces for contacting and guiding the connection member 600. The flat surfaces of the wing extensions may extend at an oblique angle to the base platform 610. As the mounting bracket 602 is moved toward the connection member 600, the wing extensions 605, 606 contact or catch the connection member 600 and adjust it about any of the axes J, K, L, to align the connection member 600 within the mounting bracket 602. The wing extensions 605, 606 may urge the connection member 600 into contact with the curved receiving surface 614 as the mounting bracket 502 moves closer to the connection member 600. With the connector body 604 positioned on the receiving surface 614, the connection member 600 may be fully mounted in an operational position and configuration to the mounting bracket 602.

In some examples, movement of the wing extensions 605, 606 toward or away from each other may be controlled by biasing members 609 (e.g. springs) or by actuators such as motors. In some examples, the mounting bracket 602 may be coupled to a sensor system 616 that may include an optical sensor, a force sensor, a position sensor, a velocity sensor, an accelerometer or other types of sensors for monitoring the proximity and engagement of the connection member 600 with the mounting bracket 602. A sensor signal from the sensor system 616 may be used to control movement of the wing extensions 605, 606. In some examples, a control mechanism 618 (which may be part of the control system 224) may actuate movement of the wing extensions 605, 606 in coordination with a float operation of the manipulator assembly to which the mounting bracket 602 may be coupled. The float operation can be performed when control mechanism 618 signals the instrument manipulator 208 to adjust location, orientation and/or angle of manipulator assembly 200 (e.g., movement in directions A1, B1, C1, D1, E1, and/or E2 as shown in FIG. 2B). This may occur by actuating robotic control, by manual intervention by an operator, or a combination thereof as described above for FIG. 2B.

In some examples, when the mounting bracket 602 is not in contact with the connection member 600, the wing extensions 605, 606 may be in a fully extended configuration in which the gap 612 is at a larger (e.g., maximum) size. As the wing extensions 605, 606 begin to touch the connection member 600, the wing extensions 605, 606 may be move toward each other, either separately or in unison, to narrow the gap 612 and urge the connection member 600 into the fully mated configuration with the receiving surface 614. In an alternative example, when the mounting bracket 602 is not in contact with the connection member 600, the wing extensions 605, 606 may be biased toward each other by biasing members 609 such that the gap 612 is smaller (e.g., minimized). As the mounting bracket 602 moves closer to the connection member 600 and wing extensions 605, 606 begin to contact the connection member 600, the force of the biasing members 609 may be overcome and the wing extensions 605, 606 may separate, increasing the size of the gap 612. The bias force of the biasing members 609 may cause the wing extensions 605, 606 to orient the connection member 600 into alignment with the receiving surface 614.

Figure 9:
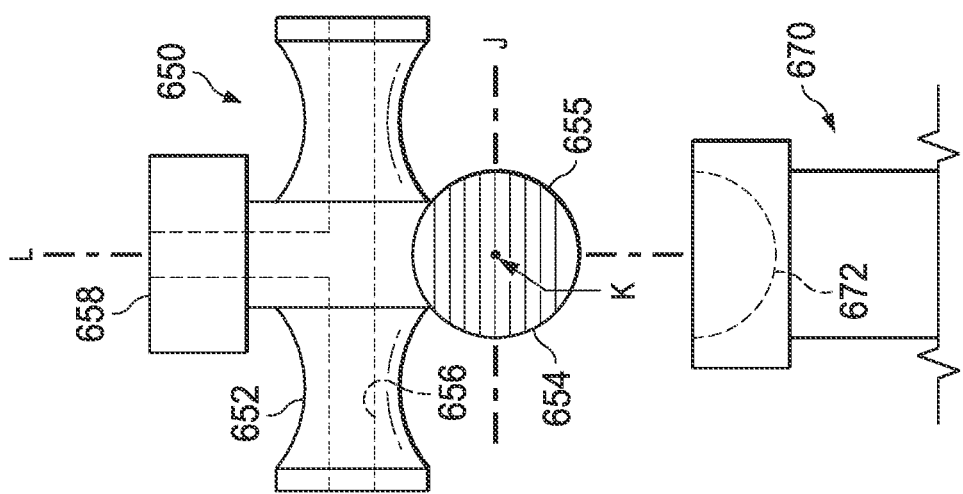
FIG. 9 illustrates a connection member and a mounting bracket with an at least partially spherical surface according to some examples.

FIG. 9 is a side view of a connection member 650 which includes a connector body 652 from which extends a coupling member 654. In some examples, the connection member 650 may be used as the connection member 216. The coupling member 654 may include a curved external surface 655 such as a spherical or partially spherical (e.g., hemispherical) surface. The connector body 652 may have a through passage 656 sized for receipt of a medical instrument. The connector body 652 may also include a port 658 for connecting to a ventilator device. The connection member 650 is configured to engage a mounting bracket 670 which may include a curved interior surface such as a partially spherical interior surface 672 sized to receive the coupling member 654 in pivoting engagement. In some examples, the coupling member 654 may engage with the surface 672 of the mounting bracket 670 and may be pivotable in multiple degrees of freedom. For example, the coupling member 654 may pivot about the axis J approximately 180-270 degrees. For example, the coupling member 654 may pivot about the axis L approximately 360 degrees. For example, the coupling member 654 may pivot about the axis K (axis K is perpendicular to the page) approximately 180-270 degrees. In alternative examples, the mounting bracket may include an external curved surface engaged with an interior curved surface of the coupling member.

FIG. 10A is a side view of a connection member 700 which includes a connector body 702 from which extends a coupling member 704. In some examples, the connection member 700 may be used as the connection member 216. The coupling member 704 may include a curved external surface 705 such as a spherical or partially spherical (e.g., hemispherical) surface. A plurality of projections 707 or other engagement features may extend from the external surface 705. The connector body 702 may have a through passage 706 sized for receipt of a medical instrument. The connector body 702 may also include a port 708 for connecting to a ventilator device. The connection member 700 is configured to engage a mounting bracket 710 which may include a curved interior surface 712 such as a partially spherical interior surface sized to receive the coupling member 704 in pivoting engagement. A plurality of recesses 713 or other engagement features may be formed in the interior surface 712. In some examples, the projections 707 may be discrete curved bumps sized to engage with recesses 713 in the form of discrete dimples. As the coupling member 704 engages with the mounting bracket 710, the projections 707 may engage the recesses 713, creating a frictional engagement between the surfaces 705, 712 that provides a resistance or limited fixation, but not necessarily a full impediment to pivotal movement between the surfaces. The frictional engagement may also enhance the connection strength. Because of the discrete projections and recesses, pivotal motion may be indexed between discrete positions allowing different predetermined orientations between the connection member 700 and the mounting bracket 710. In alternative examples, the projections 707 may be spikes, elongated ridges, circumferential bands, or other types of projections that may mate with correspondingly shaped recesses 713 in the mounting bracket to provide limited fixation and/or indexed motion. In some examples, the engagement of the projections 707 with the recesses 713 may provide tactile confirmation of engagement of the connection member 700 and the mounting bracket 710. In some alternative examples, a plurality of features on the internal surface 712 of the mounting bracket 710 may be convex projections and a plurality of features 707 on the curved external surface 705 of coupling member 704 may have a concave geometry.

FIG. 10B illustrates an alternative mounting bracket 720 which may be substantially similar to mounting bracket 710 with the differences as described. In this example, the mounting bracket 720 includes engagement features 722 in the form of linear guides which may constrain movement of the plurality of projections 707 of the coupling member 704 to linear motion relative to the mounting bracket 720.

FIG. 10C illustrates an alternative mounting bracket 730 which may be substantially similar to mounting bracket 710 with the differences as described. In this example, the mounting bracket 730 includes engagement features 732 in the form of rotational guides which may constrain movement of the plurality of projections 707 of the coupling member 704 to rotational motion relative to the mounting bracket 720.

FIGS. 11A and 11B illustrate a connection member 750 in a neutral configuration and a mounting bracket 752. The connection member 750 may rotatably or swivelly couple to the mounting bracket 752 such that the connection member 750 can rotate about the axis J relative to the mounting bracket 752. The mounting bracket 752 may be integrated into a manipulator assembly of a robot-assisted medical system. In some examples, the connection member 750 may be used as the connection member 216 and the mounting bracket 752 may be used as the mounting bracket 218. The connection member 750 may include cylindrical or toroidal-shaped coupling members 754 and 756 connected to and separated by a flexible member 758. The flexible member 758 may include a webbing of a plurality of flexible elongated members 760 such as cables, wires, rods, or filaments that allow movement of the coupling members 754, 756 relative to each other in multiple degrees of freedom. For example, the flexible member 758 may allow the coupling member 754 to move along the axis J relative to the coupling member 756 and may allow the coupling member 754 to move transversely to the axis J relative to the coupling member 756. In some examples, the flexible member 758 may couple to and support a medical instrument 762 (e.g., a catheter) passing through the connection member 750. For example, the cables 760 may be wound or tied around the instrument 762. In other examples, the flexible member 758 may be separated from the medical instrument 762 which may be supported fully by the coupling members 754, 756. The axis J may be defined through the coupling members 754, 756, and because of the flexible nature of the flexible member 758, the medical instrument 762 may or may not be aligned with the axis J. The coupling members 754 and 756 mate with curved surfaces 770, 772, respectively, of the mounting bracket 752. The coupling members 754 and 756 may be retained magnetically, and accordingly, the coupling members 754, 756 and the mounting bracket 752 may include magnets and/or a material responsive to a magnetic field. In some such examples, the mounting bracket 752 includes magnets, while the coupling members 754 and 756 include magnets or a material responsive to a magnetic field, or vice-versa.

As the mounting bracket 752 comes into contact with the connection member 750, the flexible member 758 may deform such that the coupling member 754 magnetically engages with a curved surface 770 before the coupling member 756 engages the curved surface 772. After the coupling member 754 becomes engaged, the flexible member 758 may urge the coupling member 756 into alignment with the curved surface 772 to allow both coupling members to fully mate with the predetermined orientation of the mounting bracket 752. When magnetically attached, the coupling members 754 and 756 may rotate about the longitudinal axis J, with respect to the mounting bracket 752 and the manipulator assembly. In the example of FIG. 11, because the coupling members are moveable relative to each other, there is greater flexibility and forgiveness in the initial alignment of the mounting bracket to the coupling member.

FIG. 12 illustrates a connection member 780 and the mounting bracket 752. The connection member 780 may be substantially similar to connection member 750 except as described. In this example, the connection member 780 includes the coupling members 754, 756 connected to and separated by a flexible member 782. In this example, the flexible member 782 may be a flexible sleeve that encloses an area 784. The flexible member 782 may be transparent, semi-transparent, or opaque. The flexible member may function similar to the flexible elongate members 760 in allowing movement between the coupling members 754, 756 and consequently allowing greater flexibility in the mounting bracket mating process as compared to examples with rigidly connected coupling members. Although not shown in FIG. 12, the connection member 780 may include a second flexible member having a smaller diameter than the flexible member 782. The second flexible member may be enclosed by the flexible member 782 and may be used to support the medical instrument 762.

FIGS. 13A-13C illustrate a docking or alignment guide 800 for orienting and/or positioning a connection member 802 in a predetermined configuration in preparation for mounting with a mounting bracket 804. The mounting bracket 804 may have a mounting orientation that matches the orientation of the predetermined configuration. The connection member 802 may be substantially similar to connection member 400 or other connection members described herein. The mounting bracket 804 may be substantially similar to mounting bracket 402 or other mounting brackets described herein. The docking guide 800 may have an orientation face 806 corresponding to (e.g., matching that of) the mounting bracket 804. As shown in FIG. 13A, the docking guide 800 may encounter the connection member 802 in a position or orientation that is incompatible with mounting to the mounting bracket 804 in the predetermined configuration. As shown in FIG. 13B, the docking guide 800 may couple to the connection member 802. In some examples, the position and/or orientation of the docking guide 800 and/or the connection member 802 may be modified to match each other prior to the coupling. In some examples, the position and/or orientation of the docking guide 800 and/or the connection member 802 may be modified to match each other during the coupling action. For example, geometric features on the docking guide 800 may cause the connection member 802 to adjust its position or orientation until the components are completely connected. The connection member 802 may be pivoted about the axis J, K, and or L to achieve an orientation that matches the orientation face 806. The docking guide 800 and the connection member 802 may be fixedly coupled and have a releasable connection achieved by releasable connection systems including permanent magnets, electromagnets controlled by the control system, or mechanical connectors (such as cups, fingers, and/or claws) that may or may not be controlled by the control system. After the docking guide 800 and the connection member 802 are coupled, the docking guide 800 may reconfigure the position and orientation of the connection member 802 into an intermediate configuration that matches some, but not all, of the aspects of the predetermined configuration. For example, in the intermediate configuration, the connection member 802 may match the roll and angle of the predetermined configuration but may be positioned in a different location. The docking guide 800 may continue to reconfigure the connection member 802 until the connection member is transferred to the mounting bracket 804 in the predetermined configuration as shown in FIG. 13C. The movement of the docking guide 800 may be under manual or computer-control. In some examples, the control system (e.g., control system 224) may change a position of the mounting bracket 804 while in the mounting orientation to engage the connection member 802 in the predetermined configuration. After the connection member 802 is transferred to the mounting bracket 804, the docking guide 800 may be moved away to allow the connection member to function with the mounting bracket.

FIG. 14 illustrates a side view of patient P with attached anatomic orifice device 850. A connection member 852 is connected to the anatomic orifice device 850. In some examples, the connection member 852 may be similar to any of the connection members described herein. A manipulator assembly 854 includes a mounting bracket 856. The mounting bracket 856 may be coupled to the connection member 852 by a retractable tether 858. A retraction control device 860 may be located on the manipulator assembly 854 and/or near the mounting bracket 856 and may allow the tether 858 to be extended from the mounting bracket 856 or retracted into the mounting bracket 856. In other examples, the retraction control device 860 may be located in the connector member 852. In some examples, the tether 858 may be integrated into the mounting bracket 856 and/or manipulator assembly 854 and may be extended and manually attached to the connection member 852. When the retraction control device 860 is engaged, the tether 858 may be retracted into the mounting bracket. As the tether 858 is retracted into the mounting bracket 856, at least part of the manipulator assembly 854 may move toward the connection member 852 to advance the mounting bracket 856 into contact with the connection member 852. Sensors 862 may measure the extension, angle and orientation of the tether 858. The sensors 862 may signal to a control mechanism 864 that actuates single or multiple motors 866, 868, and/or 870 to adjust the angle, orientation, and/or position of the mounting bracket 856. The control mechanism 864 may signal the instrument manipulator (e.g., instrument manipulator 208 shown in FIG. 2B) to adjust location, orientation, and/or angle of manipulator assembly 200 (e.g., in directions A1, B1, C1, D1, E1, and/or E2 as shown in FIG. 2B). The adjustments may be performed by robot-assisted control, manual intervention by an operator, or a combination thereof.

FIGS. 15A and 15B illustrate a side view of a connection member 900 and a mounting bracket 902. The connection member 900 may be substantially similar to connection member 750 or to any other connection member described herein. The connection member 750 may include coupling members 910, 912 that have ring-shaped alignment features 911. The mounting bracket 902 includes a mounting body 904 with curved surfaces 906, 908 sized and shaped to receive the coupling members 910, 912, respectively. The mounting bracket 902 may include a tab 914 that projects from the mounting body 904 between the curved surfaces 906, 908. As shown in FIG. 15B, tab 914 may have a shape that mates with an exterior surface 905 of connection member 900. For example, the geometry of tab 914 may have a handed geometry. This handed geometry may allow connection member 900 to mount flush to the exterior surface 905 in one orientation but not flush in the reverse orientation. This geometry behavior and visual differentiation may guide the user to mate the connection member 900 in a predetermined rotation configuration for use during a procedure. The mounting bracket 902 may include a guidance system 916 that includes a pair of guidance members 918, such as guidance arms, movably mounted to the mounting body 904. The guidance members 918 may optionally provide guidance for aligning of the mounting bracket 902 with the connection member 900. For example, as the mounting bracket 902 is moved into the proximity of the connection member 900, one or both of the guidance members 918 may provide visual guidance for position and orientation alignment of the mounting bracket 902 with the connection member 900. As shown in FIG. 15B, the guidance members 918 may pivot into the alignment features 911, such as when the mounting bracket 902 draws toward the connection member 900. Additionally, the tab 914 may be inserted under the coupling member 910, providing a support surface that orients the coupling member 910 for aligned engagement with the curved surface 906. With the guidance members 918 both engaged with the alignment features 911, the mounting bracket 902 may be in a fully engaged orientation and position with the connection member 900. After the mounting bracket 902 is fully engaged with the connection member 900, the guidance members 918 may optionally rotate back, such as to make room for a medical instrument to be inserted through the central passage of the coupling members 910.

FIG. 16 illustrates a hollow, curvilinear structure 950 that may be mounted to a proximal portion 952 of an anatomic orifice device 954 to arrange the anatomic orifice device in a predetermined configuration, such as an S-bend, suitable for engagement with a connection member or otherwise with a manipulation assembly. An S-bend may provide for improved user ergonomics while reducing loads on the anatomic orifice device and allowing a connection member to be positioned closer to the patient's mouth (while avoiding contact with the patient's nose or other facial features). In some examples, the hollow, curvilinear structure 950 may be in the form of a unitary sleeve. In other examples, the hollow, curvilinear structure 950 may be in a 2-part or multipart configuration. In some examples, the structure 950 may have a rigid, preformed configuration and may slide over the proximal portion 952 of the anatomic orifice device 954 to arrange the anatomic orifice device in the predetermined configuration defined by the preformed configuration of the structure 950. In some examples, the structure 950 may lock to the anatomic orifice device 954 using any of a variety of locking mechanisms including, for example, clips, hinges, snap mechanisms, or projections within mating recesses. In other examples, the structure 950 may be flexible for mounting to the proximal end 952 but may be bent, rigidized, or otherwise set into the preformed configuration after coupling to the proximal end 952. In one example of the structure 950, the curvilinear shape may be modified or bent with application of manual force and may hold its modified or bent shape when the force is released. In another embodiment, the user may initiate a mechanical, electrical or chemical change that modifies the structural behavior of the hollow curvilinear structure 950 to allow it to change shape and then return to a rigid state with or without a second user input. The structure 950 may accommodate a range of anatomic orifice sizes and geometries.

FIG. 17 is a flowchart illustrating an example method 1000 of connecting a patient to a medical instrument controlled by a manipulator assembly. The method 1000 is illustrated as a set of operations or processes 1002 through 1008. The processes illustrated in FIG. 17 may be performed in a different order than the order shown in FIG. 17, and one or more of the illustrated processes might not be performed in some embodiments of method 1000. Additionally, one or more processes that are not expressly illustrated in FIG. 17 may be included before, after, in between, or as part of the illustrated processes. In some embodiments, one or more of the processes of method 1000 may be implemented, at least in part, in the form of executable code stored on non-transitory, tangible, machine-readable media that when run by one or more processors (e.g., the processors of a control system) may cause the one or more processors to perform one or more of the processes.

At a process 1002, an anatomic orifice device may be inserted into a patient anatomy. In some examples, the patient anatomy may be a patient trachea, lung, colon, intestines, kidneys and kidney calices, brain, heart, circulatory system including vasculature, and/or the like. If the patient anatomy is the trachea and/or lung, the anatomic orifice device may an airway management device such an ET tube or an LMA. The anatomic orifice device may be implemented as any of those described herein.

At a process 1004, a connection member, including any of those described herein, may be coupled to the anatomic orifice device. In some examples, a sleeve such as structure 950 may be attached to the anatomic orifice to configure the anatomic orifice device in a preferred configuration prior to coupling the connection member.

At a process 1006, a mounting bracket of a manipulator assembly may be connected to the connection member. The mounting bracket of may take the form of any of the mounting brackets described herein. The mounting bracket may be transported to and coupled to the connection member using any of the techniques described herein to align the positions and orientations of the mounting brackets and the connection members. In some examples, the mounting bracket may be driven by a robot-assisted medical system, and in other examples the mounting bracket may be moved or adjusted by direct operator control. In other examples, the movement of the mounting bracket may be controlled by a combination of robot-assisted medical system and direct operator control.

At a process 1008, a medical instrument such as a medical instrument including an elongated device, may be inserted through the connection member and into the anatomic orifice device.

In some examples a connection member may include a predetermined bent passageway that may provide for improved user ergonomics while reducing loads on an attached endotracheal tube and allowing the connection member to be positioned closer to the patient's mouth (while avoiding contact with the patient's nose or other facial features). The predetermined bent passageway through the connection member may cause an S-bend to be formed by the connection member and the endotracheal tube. FIG. 18A illustrates a connection member 1050 engaged with a mounting bracket 1052. The mounting bracket 1052 may be similar to any of the mounting brackets described herein. FIG. 18B illustrates a cross-sectional view of the connection member 1050. The connection member 1050 may include a cylindrical or toroidal-shaped proximal coupling member 1054 and a cylindrical or toroidal-shaped distal coupling member 1056 extending on opposite ends of a connector body 1058. The coupling members 1054, 1056 may be similar to any of the coupling members described herein The connection member 1050 may also include a swivel port member 1060 that swivels about the body 1058. The swivel port member 1060 may couple with an adaptor 1061 to facilitate coupling of a pressure source (not shown) such as a ventilator. The connector body 1058 may include an internal passage 1062 including a proximal end portion sized and shaped to receive a seal assembly 1064. In some examples, the seal assembly 1064 may include seal components as described in International Publication No. WO2019/222003, filed May 8, 2019 and incorporated herein by reference in its entirety. A distal end portion of the internal passage 1062 may be sized and shaped to receive an anatomic orifice coupling member 1066 that may be attached to and rotatable relative to the connector body 1058. The anatomic orifice coupling member 1066 may couple to an anatomic orifice device such as an endotracheal tube 1068.

The internal passage 1062 may be bent to allow for a more ergonomic introduction of instruments and tools into the proximal end of the internal passage while reducing loads on the endotracheal tube 1068 that may occur with a relatively straight internal passage. An axis F1 may extend through the proximal coupling member 1054 and a proximal passage portion 1055 of the passage 1062. An axis F2 may extend through the distal coupling member 1056 and a distal passage portion 1057 of the passage 1062. In some examples the axes F1 and F2 may intersect at an angle $\theta_F$ which may be between approximately 0 and 90 degrees and in some examples angle $\theta_F$ may be between approximately 15 to 20 degrees. In some examples, the angle may be approximately 18 degrees. In some examples, the intersection of the axes F1 and F2 may be located within the portion of passage 1062 that extends through the distal coupling member 1056.

FIG. 19 illustrates the connector body 1058 in greater detail, and FIG. 20 illustrates the swivel port member 1060 in greater detail. The connector body 1058 may include proximal outer threads 1070 that threadedly couple with proximal coupling member 1054 and distal outer threads 1072 that threadedly couple with distal coupling member 1056. Between the threads 1070, 1072 a circumferential or partially-circumferential recessed channel 1074 may be formed in the body 1058. One or more apertures 1076 may extend through the recessed channel 1074 providing fluid passage from the recessed channel 1074 to the internal passage 1062. For example, the connector body 1058 may include one or more apertures 1076 (e.g., three apertures as shown in FIG. 18B and FIG. 19) on a first side of the connector body 1058 and one or more apertures (e.g., three) on a second (e.g., opposite) side of the connector body 1058. The aperture(s) may be positioned so that they do not interfere with insertion of a medical instrument (e.g., medical instrument 1092 shown in FIG. 21) through the internal passage 1062. As shown in FIG. 20, the swivel port member 1060 may include a port portion 1078 and ring portion 1080 bounding an open area 1082. An aperture 1084 in the ring portion 1080 provides fluid passage from the port portion 1078 to the open area 1082. As shown in FIGS. 18A and 18B, the ring portion 1080 encircles the recessed channel 1074 creating a flow passage 1086. Fluid, such as air, provided through the port portion 1078 from a ventilator may flow through the aperture 1084 into the flow passage 1086. From the flow passage 1086, the fluid may flow through the aperture(s) 1076 and into the internal passage 1062. From the internal passage 1062, the fluid may flow through the endotracheal tube 1068 and into the patient anatomy.

With reference to FIGS. 18A and 18B, the connection member 1050 may be magnetically coupled to the mounting bracket 1052 as described in previous examples and may have a limited rotation about the axis F1 relative to the mounting bracket 1052 while the connection member 1050 remains translationally static relative to the mounting bracket 1052. The anatomic orifice coupling member 1066 and the endotracheal tube 1068 to which it is fixed may rotate, at least partially, about the axis F2 relative to the connector body 1058. The swivel port member 1060 may rotate, at least partially, about the axis F1 relative to the connector body 1058. The adaptor 1061 may rotate, at least partially, about the axis F3 relative to the port portion 1078. Seal passages 1087, 1088, 1089 may accommodate o-rings or other types of seal devices that minimize fluid leaking as the various components swivel and rotate. The swivel and rotation motions may occur in response to even slight movement of the patient or manipulator assembly. Larger patient movement may generate a force that causes the release of the coupling members 1054, 1056 from the bracket 1052. Thus, the connection member 1050 coupled to the endotracheal tube 1068 may separate from the bracket 1052.

FIG. 21 is an illustration of a clinical environment in which a patient 1090 is situated on a table with the endotracheal tube 1068 inserted through the mouth of patient 1090. The endotracheal tube 1068 may be coupled to the connection member 1050, which may be coupled to a pressurized gas source (e.g., ventilator, not shown) that may provide a gas through the connector body 1058, into the endotracheal tube 1068, and into the patient 1090 (e.g. to the lungs of patient 1090). An elongated medical instrument 1092 (e.g., medical instrument 118) may be inserted through the connection member 1050 and endotracheal tube 1068 and into the patient 1090. The elongated medical device 1092 may be coupled to a manipulating system 1094, such as the manipulator assembly 1102 shown in FIG. 22. The mounting bracket 1052 may be coupled to a spar, which may be coupled to a manipulating arm 1095, which may include a plurality of links that may be coupled by one or more joints. The arm 1095 may be mounted to a base or alternatively may be mounted on a surgical table, ceiling, wall, or floor. The medical instrument 1092 may be coupled to an instrument carriage 1097, which may translate on the arm 1095, and may optionally also rotate the instrument in response to user control inputs. The system may be operatively coupled to a control system (see FIG. 22), which may be used to adjust the position of instrument 1092 or to advance or retract the instrument 1092. For example, an instrument 1092 may be inserted through the connector body 1058 and endotracheal tube 1068 and into the patient's lung to allow for performance of a biopsy procedure or other procedure. Performance of a clinical procedure in the lungs may require ventilation through the ventilator adaptor 1061. With the internal passage 1062 bent, a lower, more ergonomic introduction of instrument 1092 (or additional instruments through one or more working channels of instrument 1092) may be permitted while reducing loads on the endotracheal tube 1068 that may otherwise occur with a relatively straight internal passage. For example, the arm 1095 may be positioned in a more horizontal position relative to the patient or table using a connection member 1050 with a bent internal passage 1062 than with a connection member having a straight internal passage.

In some embodiments, the systems and methods disclosed herein may be used in a medical procedure performed with a robot-assisted medical system as described in further detail below. As shown in FIG. 22, a robot-assisted medical system 1100 may include a manipulator assembly 1102 (e.g., manipulator assembly 126, 200) for operating a medical instrument 1104 in performing various procedures on a patient P positioned on a table T in a surgical environment 1101. The medical instrument 1104 may correspond to the instrument 118, 214, or any medical instrument described herein. The manipulator assembly 1102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. A master assembly 1106, which may be inside or outside of the surgical environment 1101, generally includes one or more control devices for controlling manipulator assembly 1102. Manipulator assembly 1102 supports medical instrument 1104 and may optionally include a plurality of actuators or motors that drive inputs on medical instrument 1104 in response to commands from a control system 1112. The actuators may optionally include drive systems that when coupled to medical instrument 1104 may advance medical instrument 1104 into a naturally or surgically created anatomic orifice. Other drive systems may move the distal end of medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 1104 for grasping tissue in the jaws of a biopsy device and/or the like.

Robot-assisted medical system 1100 also includes a display system 1110 for displaying an image or representation of the surgical site and medical instrument 1104 generated by a sensor system 1108 which may include an endoscopic imaging system. Display system 1110 and master assembly 1106 may be oriented so an operator O can control medical instrument 1104 and master assembly 1106 with the perception of telepresence. Any of the previously described graphical user interfaces may be displayable on a display system 1110 and/or a display system of an independent planning workstation.

In some embodiments, medical instrument 1104 may include components for use in surgery, biopsy, ablation, illumination, irrigation, or suction. Optionally medical instrument 1104, together with sensor system 1108 may be used to gather (e.g., measure or survey) a set of data points corresponding to locations within anatomic passageways of a patient, such as patient P. In some embodiments, medical instrument 1104 may include components of the imaging system which may include an imaging scope assembly or imaging instrument that records a concurrent or real-time image of a surgical site and provides the image to the operator or operator O through the display system 1110. In some embodiments, imaging system components may be integrally or removably coupled to medical instrument 1104. However, in some embodiments, a separate endoscope, attached to a separate manipulator assembly may be used with medical instrument 1104 to image the surgical site. The imaging system may be implemented as hardware, firmware, software or a combination thereof which interact with or are otherwise executed by one or more computer processors, which may include the processors of the control system 1112.

The sensor system 1108 may include a position/location sensor system (e.g., an electromagnetic (EM) sensor system) and/or a shape sensor system for determining the position, orientation, speed, velocity, pose, and/or shape of the medical instrument 1104.

Robot-assisted medical system 1100 may also include control system 1112. Control system 1112 includes at least one memory 1116 and at least one computer processor 1114 for effecting control between medical instrument 1104, master assembly 1106, sensor system 1108, and display system 1110. Control system 1112 also includes programmed instructions (e.g., a non-transitory machine-readable medium storing the instructions) to implement a plurality of operating modes of the robot-assisted medical system including a navigation planning mode, a navigation mode, and/or a procedure mode. Control system 1112 also includes programmed instructions (e.g., a non-transitory machine-readable medium storing the instructions) to implement some or all of the methods described in accordance with aspects disclosed herein, including, for example, moving a mounting bracket coupled to the manipulator assembly to the connection member, processing sensor information about the mounting bracket and/or connection member, and providing adjustment signals or instructions for adjusting the mounting bracket.

Control system 1112 may optionally further include a virtual visualization system to provide navigation assistance to operator O when controlling medical instrument 1104 during an image-guided surgical procedure. Virtual navigation using the virtual visualization system may be based upon reference to an acquired pre-operative or intra-operative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions. Not all the illustrated processes may be performed in all embodiments of the disclosed methods. Additionally, one or more processes that are not expressly illustrated in may be included before, after, in between, or as part of the illustrated processes. In some embodiments, one or more of the processes may be performed by a control system or may be implemented, at least in part, in the form of executable code stored on non-transitory, tangible, machine-readable media that when run by one or more processors may cause the one or more processors to perform one or more of the processes.

Any alterations and further modifications to the described devices, instruments, methods, and any further application of the principles of the present disclosure are fully contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The systems and methods described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like. While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

This disclosure describes various instruments, portions of instruments, and anatomic structures in terms of their state in three-dimensional space. As used herein, the term position refers to the location of an object or a portion of an object in a three-dimensional space (e.g., three degrees of translational freedom along Cartesian x-, y-, and z-coordinates). As used herein, the term orientation refers to the rotational placement of an object or a portion of an object (e.g., in one or more degrees of rotational freedom such as roll, pitch, and/or yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object.

While certain illustrative embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
    a connection member configured to be connected to an anatomic orifice device, the anatomic orifice device configured for insertion into a patient; and
    a mounting bracket coupled to a robot-assisted medical system, the mounting bracket including a movable mounting component coupled to a fixed mounting component, the movable mounting component having a first configuration for mounting to the connection member in a first engagement and a second configuration for mounting to the connection member in a second engagement,
    wherein the connection member is spaced apart from the fixed mounting component and in direct contact with the movable mounting component in the first engagement and is in direct contact with the movable mounting component and the fixed mounting component in the second engagement.

2. The system of claim 1, wherein the movable mounting component includes a spring-loaded platform.

3. The system of claim 1, further comprising a motor, wherein the movable mounting component is movable by the motor.

4. The system of claim 1, wherein the movable mounting component includes a curved platform.

5. The system of claim 1, wherein the fixed mounting component includes a curved platform.

6. The system of claim 1, wherein the movable mounting component includes a magnet.

7. The system of claim 1, wherein the fixed mounting component includes a magnet.

8. The system of claim 7, wherein the magnet includes an electromagnet.

9. The system of claim 1, further comprising an eject mechanism configured to move the movable mounting component to release the connection member.

10. The system of claim 9, further comprising a motor, and wherein the eject mechanism is actuatable by the motor.

11. The system of claim 1, wherein the movable mounting component includes a pair of arms.

12. The system of claim 11, wherein at least one arm of the pair of arms includes a curved surface.

13. The system of claim 11, wherein a connection member contact surface of at least one arm of the pair of arms is at an oblique angle with respect to the fixed mounting component.

14. The system of claim 11, wherein the pair of arms are configured to retract in unison.

15. The system of claim 11, wherein the pair of arms are spring-loaded.

16. The system of claim 11, wherein the pair of arms are actuatable by one or more motors.

17. The system of claim 11, wherein the fixed mounting component extends between the pair of arms.

18. The system of claim 1, wherein the fixed mounting component includes a groove shaped to mate with a corresponding feature of the connection member.

19. The system of claim 1, wherein the fixed mounting component includes a projection shaped to mate with a corresponding feature of the connection member.

20. The system of claim 1, further comprising a hollow curvilinear structure configured to attach to the anatomic orifice device to position the anatomic orifice device in a predetermined configuration.

21. The system of claim 20, wherein the hollow curvilinear structure is rigid.

22. The system of claim 20, wherein the hollow curvilinear structure is bendable.

23. The system of claim 20, wherein the predetermined configuration includes an S-bend.

24. The system of claim 20, wherein the hollow curvilinear structure is a unitary structure.

25. The system of claim 20, wherein the hollow curvilinear structure includes a first component coupled to a second component.

* * * * *